(12) United States Patent
Ceriani et al.

(10) Patent No.: US 6,190,885 B1
(45) Date of Patent: Feb. 20, 2001

(54) FUSION PROTEIN CONTAINING HMFG EPITOPE(S)

(75) Inventors: Roberto L. Ceriani; Jerry A. Peterson, both of Lafayette; David J. Larocca, Encinitas, all of CA (US)

(73) Assignee: Cancer Research Fund of Contra Costa, San Francisco, CA (US)

( * ) Notice: Under 35 U.S.C. 154(b), the term of this patent shall be extended for 0 days.

(21) Appl. No.: 08/134,198

(22) Filed: Oct. 8, 1993

Related U.S. Application Data

(63) Continuation-in-part of application No. 08/046,103, filed on Apr. 8, 1993, now Pat. No. 5,532,135, which is a continuation of application No. 07/473,673, filed on Feb. 2, 1990, now abandoned.

(51) Int. Cl.[7] ............................ C12P 21/04; C12P 21/06; A61K 38/00; C07K 16/00
(52) U.S. Cl. ...................... 435/69.7; 435/69.1; 435/69.8; 435/71.1; 530/324; 424/192.1
(58) Field of Search ................................ 530/350, 324, 530/395, 412; 435/69.1, 69.7, 69.8, 71.1, 69.3, 70.1, 172.1

(56) References Cited

U.S. PATENT DOCUMENTS

| | | |
|---|---|---|
| 4,376,110 | 3/1983 | David et al. . |
| 4,486,530 | 12/1984 | David et al. . |
| 4,584,268 * | 4/1986 | Ceriani et al. . |
| 4,632,901 | 12/1986 | David et al. . |
| 4,745,055 * | 5/1988 | Schenk et al. . |
| 4,774,175 | 9/1988 | Chang et al. . |
| 4,963,484 * | 10/1990 | Kufe ..................................... 435/69.3 |
| 5,075,219 | 12/1991 | Ceriani et al. . |
| 5,077,220 | 12/1991 | Ceriani et al. . |
| 5,536,647 * | 7/1996 | Ceriani et al. ...................... 435/69.1 |

OTHER PUBLICATIONS

Ceriani et al. Somat. Cell Gen. 9:415–427, 1983.*
Larocca et al. Hybridoma 11:191–201, 1992.*
Palfreyman et al. J. Immunol Meth. 75:383–393, 1984.*
Imam et al, Br.J. Cancer 3:373(1988).
Peterhans et al., Anal. Biochem. 163:470(1987).
Imam et al., Biochem. J., 193:47(1981).
Ceriani, R.L., in Mechanisms of Cancer Metastasis: Potential Therapeutic Implications, Ch. 16 "Breast Cancer Diagnosis with Human Mammary Epithelial Antigens & the Prospective Use of Antibodies in Therapy", pp. 235–257(1986).
Salinas et al., Cancer Research 47:907 (1987).
Handl et al., J. Clin. Microbiol. 26:1555–1560 (1988).
Henry, J.B., "Clinical Diagnosis & Management by Laboratory Methods", Saunders Company 1:528 (1979).
Ceriani, R.L., et al., Anal. Biochem. 201:178 (1992).
Centocor® CA 15–3 RIA, Prospectus.

* cited by examiner

*Primary Examiner*—Yvonne Eyler
(74) *Attorney, Agent, or Firm*—Viviana Amzel; Arter & Hadden, LLP

(57) ABSTRACT

A fusion protein comprises a sequence of amino acids which binds antibodies specific to the human milk fat globule (HMFG) differentiation antigens. Specific amino acid sequences are provided, and a fusion protein may be used as an immunogen and for diagnostic purposes.

23 Claims, 4 Drawing Sheets

UNCOMPETED

COMPETED

PETERHANS ASSAY

COMPLETE REACTION OR MAXIMUM VALUE

INCOMPLETE REACTION OR INTERMEDIATE VALUE
ELISA SANDWICH ASSAY (HYBRITECH PATENT)

COMPLETE REACTION (MAXIMUM VALUE)

INCOMPLETE REACTION (INTERMEDIATE VALUE)
SANDWICH ASSAY (HYBRITECH PATENT)

COMPLETE REACTION OR MAXIMUM VALUE

INCOMPLETE REACTION OR INTERMEDIATE VALUE
PRESENT RECOMBINANT ANTIGEN COMPETITIVE ASSAY

SEQUENCE LISTING (1) GENERAL INFORMATION:

(iii) NUMBER OF SEQUENCES:   42

(2) INFORMATION FOR SEQ ID NO:1:

(i) SEQUENCE CHARACTERISTICS:
      (A) LENGTH:   275 base pairs
      (B) TYPE:          nucleic acid
      (C) STRANDEDNESS: single
      (D) TOPOLOGY:  linear (ii) MOLECULE TYPE:    DNA (xi) SEQUENCE DESCRIPTION: SEQ ID NO:1:

```
CGCCTTTGGA GCAGAGAGGA GGCAATGGCC ACCATGGAGA ACAAGGTGAT         50

CTGCGCCCTG GTCCTGGTGT CCATGCTGGC CCTCGGCACC CTGGCCGAGG        100

CCCAGACAGA GACGTGTACA GTGGCCCCCC GTGAAAGACA GAATTGTGGT        150

TTTCCTGGTG TCACGCCCTC CCAGTGTGCA AATAAGGGCT GCTGTTTCGA        200

CGACACCGTT CGTGGGGTCC CCTGGTGCTT CTATCCTAAT ACCATCGACG        250

TCCCTCCAGA AGTGTCTAAG GAATT                                  275
```

(2) INFORMATION FOR SEQ ID NO:2:

(i) SEQUENCE CHARACTERISTICS:
      (A) LENGTH:   275 base pairs
      (B) TYPE:          nucleic acid (C) STRANDEDNESS: single
            (D) TOPOLOGY: linear (ii) MOLECULE TYPE:    RNA (xi) SEQUENCE DESCRIPTION: SEQ ID NO:2:

CGCCUUUGGA GCAGAGAGGA GGCAAUGGCC ACCAUGGAGA ACAAGGUGAU         50

CUGCGCCCUG GUCCUGGUGU CCAUGCUGGC CCUCGGCACC CUGGCCGAGG        100

CCCAGACAGA GACGUGUACA GUGGCCCCCC GUGAAAGACA GAAUUGUGGU        150

UUUCCUGGUG UCACGCCCUC CCAGUGUGCA AAUAAGGGCU GCUGUUUCGA        200

CGACACCGUU CGUGGGGUCC CCUGGUGCUU CUAUCCUAAU ACCAUCGACG        250

UCCCUCCAGA AGAGGAGUGU GAAUU                                    275

(2) INFORMATION FOR SEQ ID NO:3:

(i) SEQUENCE CHARACTERISTICS:
            (A) LENGTH:    280 base pairs
            (B) TYPE:           nucleic acid
            (C) STRANDEDNESS: single
            (D) TOPOLOGY: linear (ii) MOLECULE TYPE:    DNA (xi) SEQUENCE DESCRIPTION: SEQ ID NO:3:

TTCCCGCCTT TGGAGCAGAG AGGAGGCAAT GGCCACCATG GAGAACAAGG         50

TGATCTGCGC CCTGGTCCTG GTGTCCATGC TGGCCCTCGG CACCCTGGCC        100

GAGGCCCAGA CAGAGACGTG TACAGTGGCC CCCGTGAAA GACAGAATTG         150

TGGTTTTCCT GGTGTCACGC CCTCCCAGTG TGCAAATAAG GGCTGCTGTT        200

TCGACGACAC CGTTCGTGGG GTCCCCTGGT GCTTCTATCC TAATACCATC        250

GACGTCCCTC CAGAAGTGTC TAAGGAATTC                               280

(2) INFORMATION FOR SEQ ID NO:4:

(i) SEQUENCE CHARACTERISTICS:
            (A) LENGTH:    89
            (B) TYPE:           amino acids
            (C) STRANDEDNESS:
            (D) TOPOLOGY: linear (ii) MOLECULE TYPE:    peptide (xi) SEQUENCE DESCRIPTION: SEQ ID NO:4:

Phe Pro Pro Leu Glu Gln Arg Gly Gly Asn Gly His His Gly Glu
                 5                  10                  15

Gln Gly Asp Leu Arg Pro Gly Pro Gly Val His Ala Gly Pro Arg
                20                  25                  30

His Pro Gly Arg Gly Pro Asp Arg Asp Val Tyr Ser Gly Pro Pro
                35                  40                  45

Lys Thr Glu Leu Trp Phe Ser Trp Cys His Ala Leu Pro Val Cys
                50                  55                  60

Lys Gly Leu Leu Phe Arg Arg His Arg Ser Trp Gly Pro Leu Val
                65                  70                  75

Leu Leu Ser Tyr His Arg Arg Pro Ser Arg Ser Val Gly Ile
                80                  85

(2) INFORMATION FOR SEQ ID NO:5:

(i) SEQUENCE CHARACTERISTICS:

(A) LENGTH:      84
            (B) TYPE:            amino acid
            (C) STRANDEDNESS:
            (D) TOPOLOGY:    linear (ii) MOLECULE TYPE:       peptide (xi) SEQUENCE DESCRIPTION: SEQ ID NO:5:

Met Ala Thr Met Glu Asn Lys Val Ile Cys Ala Leu Val Leu Val
                 5                  10                  15

Ser Met Leu Ala Leu Gly Thr Leu Ala Glu Ala Gln Thr Glu Thr
                20                  25                  30

Cys Thr Val Ala Pro Arg Glu Arg Gln Asn Cys Gly Phe Pro Gly
                35                  40                  45

Val Thr Pro Ser Gln Cys Ala Asn Lys Gly Cys Cys Phe Asp Asp
                50                  55                  60

Thr Val Arg Gly Val Pro Trp Cys Phe Tyr Pro Asn Thr Ile Asp
                65                  70                  75

Val Pro Pro Glu Val Ser Lys Glu Phe
                80

(2) INFORMATION FOR SEQ ID NO:6:

(i) SEQUENCE CHARACTERISTICS:
            (A) LENGTH:      6
            (B) TYPE:            amino acid
            (C) STRANDEDNESS:
            (D) TOPOLOGY:    linear (ii) MOLECULE TYPE:       peptide (xi) SEQUENCE DESCRIPTION: SEQ ID NO:6:

Asp Leu Arg Pro Gly Pro
                 5

(2) INFORMATION FOR SEQ ID NO:7:

(i) SEQUENCE CHARACTERISTICS:
            (A) LENGTH:      6
            (B) TYPE:            amino acid
            (C) STRANDEDNESS:
            (D) TOPOLOGY:    linear (ii) MOLECULE TYPE:       peptide (xi) SEQUENCE DESCRIPTION: SEQ ID NO:7:

Asp Thr Arg Pro Ala Pro
                 5

(2) INFORMATION FOR SEQ ID NO:8:

(i) SEQUENCE CHARACTERISTICS:
            (A) LENGTH:      6
            (B) TYPE:            amino acid
            (C) STRANDEDNESS:
            (D) TOPOLOGY:    linear (ii) MOLECULE TYPE:       peptide (xi) SEQUENCE DESCRIPTION: SEQ ID NO:8:

Thr Arg Pro Ala Pro Gly
                 5

(2) INFORMATION FOR SEQ ID NO:9:

(i) SEQUENCE CHARACTERISTICS:

```
            (A) LENGTH:      7
            (B) TYPE:         amino acid
            (C) STRANDEDNESS:
            (D) TOPOLOGY:  linear (ii) MOLECULE TYPE:    peptide (xi) SEQUENCE DESCRIPTION: SEQ ID NO:9:

Asp Leu Arg Pro Gly Pro Gly
             5

(2) INFORMATION FOR SEQ ID NO:10:

(i) SEQUENCE CHARACTERISTICS:
            (A) LENGTH:      6
            (B) TYPE:         amino acid
            (C) STRANDEDNESS:
            (D) TOPOLOGY:  linear (ii) MOLECULE TYPE:    peptide (xi) SEQUENCE DESCRIPTION: SEQ ID NO:10:

His Thr Arg Pro Ala Leu
             5

(2) INFORMATION FOR SEQ ID NO:11:

(i) SEQUENCE CHARACTERISTICS:
            (A) LENGTH:    260 base pairs
            (B) TYPE:          nucleic acid
            (C) STRANDEDNESS:  single
            (D) TOPOLOGY:  linear (ii) MOLECULE TYPE:    DNA (xi) SEQUENCE DESCRIPTION: SEQ ID NO:11:
```

| | |
|---|---|
| GAATTCCATC ACACCCGGCC GGCATTATGA TTTTGTGTAC TCTTGAAATG | 50 |
| GTTATCTTTG TGGATGATTT TTTTTTTTAA GGTGAAACTT ACCTCATGAA | 100 |
| TAACTTGATT AAAGTAGTAG GTGATTAAAA TTTCAATAGA ATCAAATGAG | 150 |
| ACAAAAATTT TAAACTGACT CATTTGAGTT TCAACTTTAC AGTCATTGAC | 200 |
| CATAAAGCAC ACTAAAAATG TAAGTTACTT TTAAATACAT CTGAAATAAA | 250 |
| AATGGAATTC | 260 |

```
(2) INFORMATION FOR SEQ ID NO:12:

(i) SEQUENCE CHARACTERISTICS:
            (A) LENGTH:      9
            (B) TYPE:         amino acid
            (C) STRANDEDNESS:
            (D) TOPOLOGY:  linear (ii) MOLECULE TYPE:    peptide (xi) SEQUENCE DESCRIPTION: SEQ ID NO:12:

Glu Phe His His Thr Arg Pro Ala Leu
             5

(2) INFORMATION FOR SEQ ID NO:13:

(i) SEQUENCE CHARACTERISTICS:
            (A) LENGTH:          30
            (B) TYPE:         amino acid
            (C) STRANDEDNESS:
            (D) TOPOLOGY:  linear (ii) MOLECULE TYPE: peptide
```

(xi) SEQUENCE DESCRIPTION: SEQ ID NO:13:

Gly Val Thr Ser Ala Pro Asp Thr Arg Pro Ala Pro Gly Ser Thr
                 5                  10                  15

Ala Pro Pro Ala His Gly Val Thr Ser Ala Pro Asp Thr Arg Pro
                 20                  25                  30

(2) INFORMATION FOR SEQ ID NO:14:

(i) SEQUENCE CHARACTERISTICS:
        (A) LENGTH:    6
        (B) TYPE:            amino acid
        (C) STRANDEDNESS:
        (D) TOPOLOGY:  linear (ii) MOLECULE TYPE:      peptide (xi) SEQUENCE DESCRIPTION: SEQ ID NO:14:

Pro Asp Thr Arg Pro Ala
                 5

(2) INFORMATION FOR SEQ ID NO:15:

(i) SEQUENCE CHARACTERISTICS:
        (A) LENGTH:    6
        (B) TYPE:            amino acid
        (C) STRANDEDNESS:
        (D) TOPOLOGY:  linear (ii) MOLECULE TYPE:      peptide (xi) SEQUENCE DESCRIPTION: SEQ ID NO:15:

Asp Thr Arg Pro Ala Pro
                 5

(2) INFORMATION FOR SEQ ID NO:16:

(i) SEQUENCE CHARACTERISTICS:
        (A) LENGTH:    6
        (B) TYPE:            amino acid
        (C) STRANDEDNESS:
        (D) TOPOLOGY:  linear (ii) MOLECULE TYPE:      peptide (xi) SEQUENCE DESCRIPTION: SEQ ID NO:16:

Thr Arg Pro Ala Pro Gly
                 5

(2) INFORMATION FOR SEQ ID NO:17:

(i) SEQUENCE CHARACTERISTICS:
        (A) LENGTH:    6
        (B) TYPE:            amino acid
        (C) STRANDEDNESS:
        (D) TOPOLOGY:  linear (ii) MOLECULE TYPE:      peptide (xi) SEQUENCE DESCRIPTION: SEQ ID NO:17:

Arg Pro Ala Pro Gly Ser
                 5

(2) INFORMATION FOR SEQ ID NO:18:

(i) SEQUENCE CHARACTERISTICS:
        (A) LENGTH:    6
        (B) TYPE:            amino acid

```
        (C) STRANDEDNESS:
        (D) TOPOLOGY:  linear (ii) MOLECULE TYPE:     peptide (xi) SEQUENCE DESCRIPTION: SEQ ID NO:18:

Pro Ala Pro Gly Ser Thr
              5

(2) INFORMATION FOR SEQ ID NO:19:

(i) SEQUENCE CHARACTERISTICS:
        (A) LENGTH:    6
        (B) TYPE:           amino acid
        (C) STRANDEDNESS:
        (D) TOPOLOGY:  linear (ii) MOLECULE TYPE:     peptide (xi) SEQUENCE DESCRIPTION: SEQ ID NO:19:

Ala Pro Gly Ser Thr Ala
              5

(2) INFORMATION FOR SEQ ID NO:20:

(i) SEQUENCE CHARACTERISTICS:
        (A) LENGTH:    6
        (B) TYPE:           amino acid
        (C) STRANDEDNESS:
        (D) TOPOLOGY:  linear (ii) MOLECULE TYPE:     peptide (xi) SEQUENCE DESCRIPTION: SEQ ID NO:20:

Pro Gly Ser Thr Ala Pro
              5

(2) INFORMATION FOR SEQ ID NO:21:

(i) SEQUENCE CHARACTERISTICS:
        (A) LENGTH:    6
        (B) TYPE:           amino acid
        (C) STRANDEDNESS:
        (D) TOPOLOGY:  linear (ii) MOLECULE TYPE:     peptide (xi) SEQUENCE DESCRIPTION: SEQ ID NO:21:

Gly Ser Thr Ala Pro Pro
              5

(2) INFORMATION FOR SEQ ID NO:22:

(i) SEQUENCE CHARACTERISTICS:
        (A) LENGTH:    6
        (B) TYPE:           amino acid
        (C) STRANDEDNESS:
        (D) TOPOLOGY:  linear (ii) MOLECULE TYPE: peptide (xi) SEQUENCE DESCRIPTION: SEQ ID NO:22:

Ser Thr Ala Pro Pro Ala
              5

(2) INFORMATION FOR SEQ ID NO:23:

(i) SEQUENCE CHARACTERISTICS:
        (A) LENGTH:    6
```

```
        (B) TYPE:          amino acid
        (C) STRANDEDNESS:
        (D) TOPOLOGY:  linear (ii) MOLECULE TYPE:    peptide (xi) SEQUENCE DESCRIPTION: SEQ ID NO:23:

Thr Ala Pro Pro Ala His
                    5

(2) INFORMATION FOR SEQ ID NO:24:

(i) SEQUENCE CHARACTERISTICS:
        (A) LENGTH:    6
        (B) TYPE:          amino acid
        (C) STRANDEDNESS:
        (D) TOPOLOGY:  linear (ii) MOLECULE TYPE:    peptide (xi) SEQUENCE DESCRIPTION: SEQ ID NO:24:

Ala Pro Pro Ala His Gly
                    5

(2) INFORMATION FOR SEQ ID NO:25:

(i) SEQUENCE CHARACTERISTICS:
        (A) LENGTH:    6
        (B) TYPE:          amino acid
        (C) STRANDEDNESS:
        (D) TOPOLOGY:  linear (ii) MOLECULE TYPE:    peptide (xi) SEQUENCE DESCRIPTION: SEQ ID NO:25:

Pro Pro Ala His Gly Val
                    5

(2) INFORMATION FOR SEQ ID NO:26:

(i) SEQUENCE CHARACTERISTICS:
        (A) LENGTH:    6
        (B) TYPE:          amino acid
        (C) STRANDEDNESS:
        (D) TOPOLOGY:  linear (ii) MOLECULE TYPE:    peptide (xi) SEQUENCE DESCRIPTION: SEQ ID NO:26:

Pro Ala His Gly Val Thr
                    5

(2) INFORMATION FOR SEQ ID NO:27:

(i) SEQUENCE CHARACTERISTICS:
        (A) LENGTH:    6
        (B) TYPE:          amino acid
        (C) STRANDEDNESS:
        (D) TOPOLOGY:  linear (ii) MOLECULE TYPE:    peptide (xi) SEQUENCE DESCRIPTION: SEQ ID NO:27:

Ala His Gly Val Thr Ser
                    5

(2) INFORMATION FOR SEQ ID NO:28:

(i) SEQUENCE CHARACTERISTICS:
```

(A) LENGTH:         6
        (B) TYPE:      amino acid
        (C) STRANDEDNESS:
        (D) TOPOLOGY:  linear (ii) MOLECULE TYPE: peptide (xi) SEQUENCE DESCRIPTION: SEQ ID NO:28:

His Gly Val Thr Ser Ala
            5

(2) INFORMATION FOR SEQ ID NO: 29:

(i) SEQUENCE CHARACTERISTICS:
        (A) LENGTH:         6
        (B) TYPE:      amino acid
        (C) STRANDEDNESS:
        (D) TOPOLOGY:  linear (ii) MOLECULE TYPE: peptide (xi) SEQUENCE DESCRIPTION: SEQ ID NO:29:

Gly Val Thr Ser Ala Pro
            5

(2) INFORMATION FOR SEQ ID NO:30:

(i) SEQUENCE CHARACTERISTICS:
        (A) LENGTH:    6
        (B) TYPE:          amino acid
        (C) STRANDEDNESS:
        (D) TOPOLOGY:  linear (ii) MOLECULE TYPE:     peptide (xi) SEQUENCE DESCRIPTION: SEQ ID NO:30:

Val Thr Ser Ala Pro Asp
            5

(2) INFORMATION FOR SEQ ID NO:31:

(i) SEQUENCE CHARACTERISTICS:
        (A) LENGTH:    6
        (B) TYPE:          amino acid
        (C) STRANDEDNESS:
        (D) TOPOLOGY:  linear (ii) MOLECULE TYPE:     peptide (xi) SEQUENCE DESCRIPTION: SEQ ID NO:31:

Thr Ser Ala Pro Asp Thr
            5

(2) INFORMATION FOR SEQ ID NO:32:

(i) SEQUENCE CHARACTERISTICS:
        (A) LENGTH:    6
        (B) TYPE:          amino acid
        (C) STRANDEDNESS:
        (D) TOPOLOGY:  linear (ii) MOLECULE TYPE:     peptide (xi) SEQUENCE DESCRIPTION: SEQ ID NO:32:

Ser Ala Pro Asp Thr Arg
            5

(2) INFORMATION FOR SEQ ID NO:33:

```
        (i) SEQUENCE CHARACTERISTICS:
            (A) LENGTH:    6
            (B) TYPE:          amino acid
            (C) STRANDEDNESS:
            (D) TOPOLOGY:  linear (ii) MOLECULE TYPE:    peptide (xi) SEQUENCE DESCRIPTION: SEQ ID NO:33:

Ala Pro Asp Thr Arg Pro
                5

(2) INFORMATION FOR SEQ ID NO: 34:

(i) SEQUENCE CHARACTERISTICS:
            (A) LENGTH:    20
            (B) TYPE:          amino acid
            (C) STRANDEDNESS:
            (D) TOPOLOGY:  linear (ii) MOLECULE TYPE:    peptide (xi) SEQUENCE DESCRIPTION: SEQ ID NO:34:

Pro Asp Thr Arg Pro Ala Pro Gly Ser Thr Ala Pro Pro Ala His
                5                   10                  15

Gly Val Thr Ser Ala
              20

(2) INFORMATION FOR SEQ ID NO:35:

(i) SEQUENCE CHARACTERISTICS:
            (A) LENGTH:        20
            (B) TYPE:      amino acid
            (C) STRANDEDNESS:
            (D) TOPOLOGY:  linear (ii) MOLECULE TYPE:    peptide (xi) SEQUENCE DESCRIPTION: SEQ ID NO:35:

Ala Pro Pro Ala His Gly Val Thr Ser Ala Pro Asp Thr Arg Pro
                5                   10                  15

Ala Pro Gly Ser Thr
              20

(2) INFORMATION FOR SEQ ID NO:36:

(i) SEQUENCE CHARACTERISTICS:
            (A) LENGTH:    8
            (B) TYPE:          amino acid
            (C) STRANDEDNESS:
            (D) TOPOLOGY:  linear (ii) MOLECULE TYPE:    peptide (xi) SEQUENCE DESCRIPTION: SEQ ID NO:36:

Ala Pro Thr Arg Pro Ala Pro Gly
                5

(2) INFORMATION FOR SEQ ID NO: 37:

(i) SEQUENCE CHARACTERISTICS:
            (A) LENGTH:    3
            (B) TYPE:          amino acid
            (C) STRANDEDNESS:
            (D) TOPOLOGY:  linear (ii) MOLECULE TYPE:    peptide (xi) SEQUENCE DESCRIPTION: SEQ ID NO: 37:
```

```
Thr Arg Pro
        3

(2) INFORMATION FOR SEQ ID NO:38:

(i) SEQUENCE CHARACTERISTICS:
        (A) LENGTH:    5
        (B) TYPE:           amino acid
        (C) STRANDEDNESS:
        (D) TOPOLOGY: linear (ii) MOLECULE TYPE:      peptide (xi) SEQUENCE DESCRIPTION: SEQ ID NO:38:

Thr Arg Pro Ala Pro
            5

(2) INFORMATION FOR SEQ ID NO:39:

(i) SEQUENCE CHARACTERISTICS:
        (A) LENGTH:    3
        (B) TYPE:           amino acid
        (C) STRANDEDNESS:
        (D) TOPOLOGY: linear (ii) MOLECULE TYPE:      peptide (xi) SEQUENCE DESCRIPTION: SEQ ID NO:39:

Asp Thr Arg
        3

(2) INFORMATION FOR SEQ ID NO:40:

(i) SEQUENCE CHARACTERISTICS:
        (A) LENGTH:    4
        (B) TYPE:           amino acid
        (C) STRANDEDNESS:
        (D) TOPOLOGY: linear (ii) MOLECULE TYPE:      peptide (xi) SEQUENCE DESCRIPTION: SEQ ID NO:40:

Asp Thr Arg Pro
            4

(2) INFORMATION FOR SEQ ID NO:41:

(i) SEQUENCE CHARACTERISTICS:
        (A) LENGTH:    6
        (B) TYPE:           amino acid
        (C) STRANDEDNESS:
        (D) TOPOLOGY: linear (ii) MOLECULE TYPE:      peptide (xi) SEQUENCE DESCRIPTION: SEQ ID NO:41:

Asp Leu Arg Pro Gly Pro
                5

(2) INFORMATION FOR SEQ ID NO:42:

(i) SEQUENCE CHARACTERISTICS:
        (A) LENGTH:    9
        (B) TYPE:           amino acid
        (C) STRANDEDNESS:
        (D) TOPOLOGY: linear (ii) MOLECULE TYPE:      peptide
```

-continued (xi) SEQUENCE DESCRIPTION: SEQ ID NO:42:

Ala Pro Asp Thr Arg Pro Ala Pro Gly

FUSION PROTEIN CONTAINING HMFG EPITOP E (S)

This application is a Continuation-in-Part of co-pending U.S. application and Ser. No. 08/046,103, filed on Apr. 8, 1993 now issued as U.S. Pat. No. 5,532,135 and, which is a File Wrapper Continuation of co-pending U.S. application Ser. No. 07/473,673 filed on Feb. 2, 1990, now abandoned.

BACKGROUND OF THE INVENTION

1. Technical Field

This invention relates to an in vitro solid-phase competitive assay for detecting the presence of an antigenic analyte, or a binding fragment or precursor thereof in a biological sample utilizing a fusion protein of an antigenic peptide and a binding peptide, a solid support-bound antibody selectively binding the binding peptide, an antibody selectively binding the antigenic peptide, and optionally an antibody binding molecule. The present assay provides higher sensitivity and specificity than all other available assays.

2. Description of the Background

The determination of levels of different antigens in animal and human tissues took a definite turn with the development of immunoassays. The concept on which immunoassays are based is the quantitative binding of a known antigen in known quantities to an antibody in equally known quantities, and the binding of this antibody to the antigen to be used as a standard, and a comparison of this to a unknown sample comprising the antigen which will also be bound by the antibody. Antigen present in the unknown sample interfered with the initial binding of known quantities of antibody to known quantities of antigen. A key step of these assays is the separation of the bound form of the antibody or the antigen from its unbound form. Many configurations for this reaction have been proposed either as direct immunometric, competitive or displacement assays, and the like. However, to quantitate results it is in general needed to resort to hemagglutination assays, radioimmunoassays, enzyme-linked assays, and the like.

In general, in an immunoassay, a given analyte or antigen present in a animal or human tissue is or may be solubilized for mixing with the immunoassay system, and it is then compared to a solubilized known quantity of the analyte. The most common tissue analyte is blood, and more specifically serum and/or plasma from blood, but urine, cerebro-spinal fluid, different serum preparations and different animal and human tissues and fluids are also routinely assayed.

Some of the areas which have most benefited with the advent of immunoassays have been clinical chemistry, endocrinology and oncology. In endocrinology and clinical chemistry enzyme-linked assays and radioimmunoassays have been used to determine levels of hormones, proteins, and lipid metabolites, among other substances. In the field of oncology blood components, and some times tissue antigens or other molecules, indicate either the appearance of cancer or a pre-cancerous condition in animals or men. These molecules are routinely tested to monitor appearance, relapse, progression or regression of a cancer disease. These antigens or molecules are called cancer and/or tumor markers. For many years markers have been used for this purpose. An example thereof is the oncofetal antigen CEA which is used in the diagnosis of carcinomas, especially those of the colon. Other cancer markers include enzymes such as lactic dehydrogenase and alkaline phosphatase, metabolites such as prostaglandin and polyamine, proteins such as α-fetoprotein and human chorionic gonadotrophin, among others. Immunoassays of these cancer markers are now applied to the diagnosis and follow up of cancer patients.

These assays generally use as standard a partially or fully purified tissue antigen. In some occasions, however, polypeptides are synthesized in the laboratory for use as antigens. The more purified the antigenic substance used as standard for the immunoassay is, the more specific and trustworthy the assay.

A set of membrane-related antigens have been used for the diagnosis of breast cancer. The antigens were originally called human mammary epithelial antigens and antibodies to them were obtained by injection of human milk fat globule (HMFG) membranes to rabbits. These were polyconal antibodies called anti-human mammary epithelial (anti-HME) antibodies. The antibodies were prepared after repeated absorptions and were found to bind breast epithelial cells selectively. The discovery of this breast epithelial system of antigens opened many new immunologic opportunities in immunohistopathology, serum assays, radioimaging and eventually immunotherapy.

The anti-HME antibodies were shown to bind to breast epithelial cell lines as well as normal breast cells, but not to fibrocytes, vascular cells, and blood cells. A special group of breast epithelial antigens (BrE-antigens) originally called human mammary epithelial antigens (HME-ntigens), are bound by absorbed anti-serum (anti-HME serum) which were created in the rabbit. These antigens were found to have 150, 70 and 45–48 Kdalton molecular weights as established by affinity chromatography, and polyacrylamide gel electrophoresis double antibody immunoprecipitation. A similar system was shown to exist in the mouse. Mouse mammary epithelial antigens may also be detected by absorbed rabbit polyclonal antisera. These antisera also identify in the mouse mammary cell membrane components having molecular weights of 150, 70 and 45–48 Kdaltons. The antigens may be detected in either normal or neoplastic mouse mammary gland. These antigens are not detected in other normal tissue cells of mice.

Other polyclonal antisera were reported to have been produced against a step-purification of HMFG antigens. These antisera are pan-epithelial in nature and reactive only against the non-penetrating glycoprotein (NPGP) complex in contrast to the original anti-HME antibodies that bind the about 45, 70 and 150 kdalton antigens. Although the anti-HME antibodies bind before absorptions to the NPGP complex, anti-HME antibody final preparations do not recognize the NPGP complex as a result of absorptions with non-breast epithelial cells to render anti-HME specific.

HME antigens may be quantitated by an immunoassay in various human breast and non-breast cell lines and in normal breast epithelial cells. High concentrations of HME antigens were found in normal breast epithelial cells and in neoplastic cells. A protease treatment of live breast epithelial cell surfaces releases most antigens therefrom. Similar results show a 48–72 hour time lapse for full reconstitution of the normal breast epithelial cell membrane after digestion.

High levels of HME antigens are found in the sera of nude mice carrying human breast tumors. These antigens can be abolished by surgical removal of the breast tumor. Anti-HME antisera were shown to have certain specificity since other transplantable human tumors such as colon, lung and melanoma, did not increase HME antigen values in mice serum.

The specificity of the assay using anti-HME antigen serum for breast tumors was tested in a nude mouse model carrying transplantable human breast tumors and compared to the specificity of an assay for sialyl transferase levels, which is also a breast cancer marker. The levels of the enzyme which is present on the breast epithelial cell membrane and the HME antigens were measured simultaneously in the sera of nude mice grafted with human breast and non-breast tumors. Breast tumor-bearing mice had elevated levels of both serum markers. However, sialytransferase levels were also elevated in non-breast tumors while HME antigens were not. Upon surgical removal of all tumors, the presence of HME antigens declined precipitously in breast tumor-bearing nude mice while sialyl transferase levels remained elevated in both breast and non-breast tumor bearing animals. This is possibly due to surgical trauma and wound healing. The higher specificity of the HME antigen assay was thus proven at least in regard to sialyl transferase, a non-specific co-habitant of the cell membrane together with HME antigens. This indicates again that most, if not all, components of the breast epithelial cell are released into circulation by breast tumors, and that assay specificity, such as is obtained with an assay utilizing HME antigens, may be required to avoid that concurrent ailments or reactions in the tumor host interfere with the values obtained from sera with markers such as sialyl transferase.

HME antigens levels in the sera of breast cancer patients were also obtained using a slightly different radioimmunoassay (U.S. Pat. No. 4,584,268 to Ceriani and Peterson). In this assay, beads coated with polyclonal antibodies were incubated with a patient's serum, then the immobilized antigen was detected with the polyclonal antibodies labeled with biotin, and the latter detected by radiolabeled avidin. The assay was specific for positive cases of breast cancer since the sera of normal subjects, both male and female, suffering from benign diseases of the breast, carcinomas of lung and colon, neuroblastomas and melanomas yielded negative results. In contrast, 25% of Stage I primary breast carcinomas and more than 75% of disseminated breast cancer cases were found to have values above the cut off line.

To date the only complete proof of the existence of HME antigens, or any other breast epithelial antigens (BrE-antigens) in human sera with elevated values of the breast tumor markers, is provided by a very sensitive technique using in situ radioiodination of the HME antigens bound to an immobilized antibody. In contrast, only a small fraction of breast cancer patients, most of whom had elevated values of BrE antigens, gave positive results when less stringent criteria to detect BrE antigens in sera such as Western blotting were used. Elevated values of the three HMFG antigens detected by anti-HME antibodies were found in the circulation employing the in situ radioiodination approach. These antigens had 150, 70 and 45–48 Kdafton molecular weights in all breast cancer cases. Control sera from normal subjects and patients with colon and lung carcinomas were found to be negative. In addition, the antigen corresponding to one monoclonal antibody (Mc3) was also found in the sera of these patients by the in situ labeling technique. In later work, the Mc3 antigen was found to be associated with immune complexes in breast cancer patients.

Monoclonal antibodies have been used in immunoassays. However, their low binding constants and their restricted specificity are drawbacks to their use. Polyclonal antibodies, on the contrary, combine the specificities for several epitopes of the same antigen. Monoclonal antibodies were originally prepared against HMFG and also against breast tumor cells. As mentioned above, the most immunogenic of the HMFG antigens and breast cells is the NPGP complex, described for its binding to monoclonal antibody Mc1 (also called HMFG-2), and Mc5. This is the only antigen which has thus far been extensively quantitated in serum assays.

The original monoclonal antibodies against HMFG were followed by other monoclonal antibodies created in different laboratories. Immunoassays applied to obtain serum values for primary breast tumor patients and for disseminated disease patients yielded partially positive values in cases of primary breast tumors and small tumor loads. As the tumor load increased, more sera became positive.

The original anti-HMFG monoclonal antibodies, HMFG-1 and HMFG-2 bind to the NPGP complex of the HMFG. These antibodies detected the corresponding antigens in the sera of 30% and 53% of advanced cancer disease cases, respectively. These percentages are low, possibly as a result of the configuration of the assay. In addition, antigenic components with varying molecular weights between 280 and 320 Kdaltons were detected by means of Western blotting in a few of all positive sera detected by the assay. This may indicate either that fragments of the native antigen were found or that the different molecular weight components represent different polymorphic molecules of the antigen. No positives were detected by immunoblotting in any of the normal sera although threshold values were detected by immunoassay.

The DF3 monoclonal antibody also binds to the NPGP complex of the HMFG antigen system. Using this monoclonal antibody a comparison was made between the RIA and ELISA procedures. All yielded increased levels of antigen over the cut off line in more than 70% of the patients with disseminated breast cancer. In contrast thereto, slightly over 5% of normal women had values above the cut off value. Further, 47%, 40% and 27% of patients with ovarian carcinoma pancreatic carcinoma and melanoma were found to have elevated values above the cut-off line whereas ten out of 66 patients with benign liver disease also had elevated values. Patients with visceral breast cancer were found to have a higher frequency of elevated values than those with local or skin recurrences. Results from Western blotting studies were similar to those outlined above for HMFG-1 and HMFG-2 in that a few but not all patients with high immunoassay serum values of the antigen had positive immunoblots.

Another monoclonal antibody, 115D8, raised also against the NPGP complex, was utilized in a sandwich serum assay using the same monoclonal antibody for both layers. The results obtained were similar to the above. About 5% of the samples from normal breasts and benign breast disease showed values above the cut-off line. Breast cancer patients were found positive in 24% of Stage I cases, and in 21%, 43%, and 79% of Stages II through IV cases. 78% positives were found in benign liver disease, kidney disease and in pregnancy cases. A high percentage of ovarian, colorectal, prostate, lung carcinomas, melanoma and lymphoma cases also had elevated values. A good correlation of the marker with the progression or regression of the disease was found in 93% of the cases.

Another early attempt to measure the NPGP complex in circulation was attempted with the F36/22 monoclonal antibody. A similar percentage of positives which were obtained, increases with the severity of disease, as also reported in other assays.

A series of monoclonals were created by another laboratory. Out of a latter group, two named W1 and W9 were selected for also binding to the NPGP complex. Elevated levels of the complex were found in 47% of breast cancer patients with visceral metastases, these being favored over localized metastases. This assay was also positive in 4% of normal cases. Other carcinomas such as colorectal, lung, ovarian, and prostate carcinomas show elevated values of the complex in 12 to 60% of the cases. Recently, another assay using a monoclonal antibody, AB13, detected the NPGP complex in approximately half of advanced breast cancer patients.

The monoclonal antibody DF3 has been used in a commercially available double determinant assay called CA 15-3. Levels above the cut-off line in approximately 80% of advanced cancer patients and in only approximately 30% of primary breast cancer cases were found by this assay. Other authors, in contrast, reported only 13% of primary breast tumors and 72% of disseminated tumors to be positive. In a more detailed study only 24% of breast cancer patients were found to have elevated CA 15-3, while 70% to be positive were found in patients with the disseminated disease. A comparison of CEA and CA 15-3 in both primary and disseminated breast cancer samples, proved the latter to be more sensitive. This commercial assay and the ones discussed above against the heavy molecular weight component of the HMFG or NPGP complexes attain percentages of positives (sensitivities) which are at best similar to those originally reported when the presence of the HME-antigens in the circulation of breast cancer patients was established using polyconal antibodies. The specificities of the assays for the tissue of origin of the tumor are very low (the antigen(s) is almost pan-epithelial), and their specificities for disease conditions are hampered by their high values in hepatic and kidney disease, pregnancy, polymorphic expression of the antigen(s), and the like.

A common feature among the above immunoassays, either utilizing enzymes or radioactivity, is that they indicate a positive correlation between increasing tumor load and higher serum antigen levels. However, a further increase in sensitivity to improve early stage detection of the disease is still necessary. In this regard, an assay using the NPGP complex as a marker and employing the 3E1.2 monoclonal antibody was claimed to have higher sensitivity.

Of a limited number of breast cancer patients up to 68% of early stage patients were found to be positive by this assay whereas only 3% were detected by CA 15-3. The 3E1.2 assay resulted in 18% of positives for benign breast disease resulting then in a low specificity.

Ideally monoclonal antibodies for use in immunoassays would be created against BrE antigen epitopes expressed in breast neoplasias. Alterations in glycoprotein antigens on breast tumor cell membranes have been shown to involve changes in their glycosylation patterns such as substitutions or elongation of oligosaccharide chains without modification of the core sequences. One such monoclonal antibody which is carcinoma specific is B72-3. Its binding to NPGP in benign breast disease tissues was, however, shown later and some normal breast tissue. All the above monoclonal antibody immunoassays for breast cancer rely on serum levels of the NPGP complex. Other antigens, however, have been explored such as the GP-15, Mc3, and Mc8 antigens. The former is a small molecular weight BrE antigen (15 Kdalton) which is present in the cell membrane. It detects mainly, if not exclusively, breast epithelium that has undergone apocrine metaplasia. It has been found, possibly as a result of its selectivity, in the sera of approximately 40% of breast cancer patients. In addition, a small molecular weight antigen (46 Kdalton) of the HMFG system, already detected by in situ radioiodination in the sera of breast cancer patients was measured by a serum immunoassay using a sandwich configuration with monoclonal antibody Mc8 conjugated to biotin as the probing antibody to be finally detected by $^{125}$I-labeled avidin (Salinas et al, Cancer Research 47:907 (1987)).

Levels of this antigen were detected in breast cancer patients but not in normal subjects, ovarian carcinomas, colon carcinomas or osteosarcomas. Levels of the Mc3-Mc8 antigen, however, were inversely related to the tumor load. Small tumor loads were 95% positive whereas high tumor loads were 65% positive. This fact was explained by the presence of immune complexes against the antigen whose titer is increased in the high tumor load group. The presence of higher level immune complexes may accelerate clearance of the antigen from blood.

Thus, although most of the above assays employing monoclonal antibodies detect the NPGP complex of the HMFG system, many of them may bind to different epitopes. A heterogeneity of epitopic expression may create the relatively small differences seen among different assays. The diffusely pan-epithelial nature of the NPGP complex as a marker was thus established as shown by its high circulating levels found in other carcinomas, melanomas and even in leukemia. The levels obtained varied depending on the units used in different immunoassays. The percent of positives found at different stages of breast cancer are similar to those originally reported with an assay using polyclonal antibodies to other components of the HMFG. An important drawback of the assays based on the detection of the NPGP complex using monoclonal antibodies is that they lack the specificity of polyclonal assays.

A comparison of the specificities of the CEA assay, an assay detecting the NPGP complex using the Mc5 monoclonal antibody in an antigen displacement, and the original polyclonal antibody assay against HME antigens was made. The polyclonal antibody assay showed very high sensitivity and specificity. It yielded negative values for colon, ovarian, pancreatic, laryngeal and endometrial carcinomas, lymphomas, myelomas, melanomas, and leukemias. Only one case of lung carcinoma showed an elevated value. All normal serum controls were negative, thus showing this assay to have high specificity. Positive serum values for both the NPGP complex and CEA assays were not restricted to breast tumor patient's sera.

Another study reported a higher sensitivity for the polyclonal assay of the HME antigens when compared with the monoclonal antibody assay for the NPGP complex and the CEA test. These three assays were compared in terms of their follow-up ability. The response of one polyclonal antibody assay for HME antigens (cut-off 100 $\mu$g/ml) to breast cancer relapse and tumor mass change was quantitated and showed a very sensitive response, far above that demonstrated for the Mc5 assay (cut-off 10 $\mu$g/ml) for the NPGP complex. In contrast, the CEA assay either responds slowly or not at all. In clinical cases measurable shrinkage of breast tumor mass was obtained and there was a fast decrease of HME antigens corresponding to a decreased tumor mass brought about by irradiation. The levels of the NPGP complexes remained high and the CEA was unresponsive. In summary, the polyclonal assay for HME antigens has a faster response to changes, and is more accurate in predicting objective changes in tumor mass than the other two assays (CEA and NPGP complex).

Previous studies showed the prognostic power for BrE antigens to be up to 90%. A comparison of the ability of these three assays, the CEA, the NPGP complex, and the HME antigen assays, for predicting relapse was performed by comparing the ability to detect relapse within at least two months in breast cancer patients with no evidence of disease (NED) after an increase of 50% in the serum marker base line by the three methods. The HME antigen method showed a predictability of 73% while the CEA and NPGP complex methods had a 46% predictability. Clearly, among the three, the HME antigen method is the one of choice to establish prognosis due to its high predictive ability and its ability to detect early changes in tumor mass.

U.S. Pat. No. 4,376,110 to David discloses a competitive assay utilizing two antibodies, one of which may be bound to a solid support. The two antibodies compete for the analyte in the sample and may bind to different epitopes of the analyte. The David assay could not be adapted to utilize a fusion protein, even if considered desirable, since the only antigenic substrate present is the analyte, and it cannot be replaced. The prior art assay may be an ELISA or sandwich assay, both of which are depicted in FIGS. 2 and 3 of this patent. The assay of U.S. Pat. No. '110, in addition, requires that the analyte be bound to the free antibody first and, that this free antibody be labeled. Thus the prior art assay produces a soluble labeled analyte-antibody complex, which is totally absent from the present assay, and the amount of label bound to the solid support is proportional to the amount of analyte in the sample whereas in the present assay it is inversely proportional to it.

Other assays utilizing fusion proteins are known in the art. However, they are all different from the present in vitro competitive heterogeneous assay. The following are examples known to the inventors.

Peterhans et al disclose a competitive assay utilizing a fusion protein of β-galactosidase and interferon (Peterhans et al, Analytical Biochemistry 163; 470–475(1987)). That assay uses only one type of antibody, which in this case is bound to a solid support, and a fusion protein and the analyte in the sample, both in solution compete for that antibody. In the Peterhans assay, an anti-interferon-α monoclonal antibody is attached to the solid support and then incubated with the fusion protein diluted in the sample containing interferon (the analyte). The solid supported material remaining after this step is then incubated in the presence of o-NO$_2$-phenyl-glactopyranose (a substrate for β-galactosidase) to determine the amount of fusion protein bound to the antibody and compared with the results obtained by conducting the in the absence of the sample. Although being a competitive assay relying on the use of a fusion protein made of two polypeptides (β-galactosidase and interferon), the prior art assay only utilizes one antibody selectively binding to only one of the two portions of the fusion protein, in this case in solution together with the analyte. FIG. 1 of this patent shows the assay graphically. The prior art assay does not add the fusion protein to a solid phase prior to conducting the competitive portion of the assay is done in the present assay. Both the fusion protein and the sample containing the analyte are added in the same step, and the competitive step is conducted with a solid supported antibody and a fusion protein free in solution whereas the present assay requires a solid supported fusion protein and a free antibody.

In another case, U.S. Pat. No. 4,745,055 to Schenk et al, human surfactant azoprotein (HSA) was determined using an assay configuration similar to the above and a second assay anti-HSA antibody interfered with the β-galactosidase activity of the fusion protein.

Handl et al disclose another competitive assay relying on the utilization of a fusion protein (Handl et al, J.Clin.Microbiol.26:1555–1560(1988)). The fusion protein in this case is composed of β-galactosidase and enterotoxin II and is bound to a solid support. A test sample containing enterotoxin II (the analyte) is added to the solid supported fusion protein, and anti-enterotoxin polyclonal antibodies are then added and both the fusion protein and the enterotoxin II in the sample are allowed to compete for the polyclonal antibodies. The amount of anti-enterotoxin antibody bound to the solid supported fusion protein is determined by adding anti-antibody immunoglobulin which is labeled with alkaline phosphatase. A substrate for the enzyme alkaline phosphatase is then added to the solid supported material and the amount of conversion obtained is compared with that obtained from a similar test conducted in the absence of the test sample. Although this is also a competitive test utilizing a fusion protein and a sample containing the analyte, both capable of binding the antibody, it is different from the assay of the invention in that the fusion protein is bound to the solid support by the β-galactosidase portion thereof, and it only utilizes one type of antibody binding the antigenic peptide portion of the fusion protein. Accordingly, neither the Peterhans nor the Handl assays have the fusion protein in a sandwich form as is the competitive assay of the invention.

Antibodies against HTLV-III were measured in U.S. Pat. No. 4,774,175 to Chang, T. W. et al., using a fusion protein carrying determinants of the virus fixed onto a solid phase.

The above studies show that determination of markers in a clinical setting can be improved by providing an assay of higher sensitivity and/or specificity (above 95%). Such assay will increase clinical diagnosis accuracy by using markers specific for, e.g., different types of cancer and the endocrine system, among others, provided that the markers can be obtained with substantial purity to develop antibodies against them of high avidity and specificity.

SUMMARY OF THE INVENTION

This invention relates to an in vitro solid-phase, competitive assay for detecting the presence of a peptide analyte or functional fragment or precursor thereof in a biological sample, comprising contacting a fusion protein comprising a binding peptide and an antigenic peptide or functional fragment or precursor thereof with an antibody which selectively binds to a site of the binding peptide which is absent from the antigenic peptide while the antigenic peptide portion thereof remains free, the antibody being covalently bound to a polyamino acid-coated solid support;

adding thereto a biological sample suspected of comprising a peptide analyte or functional fragment or precursor thereof;

adding thereto an antibody capable of selectively binding to the analyte peptide or fragment or precursor thereof and to a site of the antigenic peptide that is absent from the binding peptide, and allowing the antibody to bind any free peptide analyte or fragment or precursor thereof present in the sample and the free antigenic peptide portion of the solid supported fusion protein to form analyte-antibody or solid supported fusion protein-antibody complexes; and determining the amount of solid supported anti-antigenic peptide antibody present and comparing it to the amount of solid supported antibody present in a control assay, whereby when the amount of peptide analyte in the sample increases the amount of solid supported antibody decreases.

This invention also relates to an in vitro solid-phase, competitive assay for determining the presence of neoplastic tissue from a solid tumor or metastasis thereof in a biological sample, comprising contacting a fusion protein comprising a binding peptide and an antigenic peptide of a epithelial mammary cell or functional fragment or precursor thereof with an antibody which selectively binds to a site of the binding peptide which is absent from the antigenic peptide while the antigenic peptide portion thereof remains free, the antibody being covalently bound to a polyamino acid-coated solid support;

adding thereto a biological sample suspected of comprising neoplastic cells from a solid tumor or metastasis thereof or functional fragment or precursor thereof;

adding thereto an antibody capable of selectively binding to an antigen of the neoplastic cell or fragment or precursor thereof and to a site of the antigenic peptide that is absent from the binding peptide, and allowing the antibody to bind any free peptide analyte or fragment or precursor thereof present in the sample and the free antigenic peptide portion of the solid supported fusion protein to form neoplastic cell antigen-antibody or solid supported fusion protein-antibody complexes;

adding thereto a labeled antibody-binding molecule and allowing the labeled molecule to bind the double antibody-fusion protein solid supported complex to form a labeled molecule-double antibody-fusion protein solid supported complex; and determining the amount of solid supported label present and comparing it to the amount of solid supported label present in a control assay, whereby when the amount of peptide analyte in the sample increases the amount of solid supported label decreases.

Also provided herein is a fusion protein comprising a binding peptide or fragment thereof and an antigenic peptide comprising an antigen of epithelial mammary cell or fragment or precursor thereof, the binding peptide capable of being bound by a first monoclonal antibody through a site that is absent from the antigenic peptide and lacking a site of the antigenic peptide that is capable of being bound by a second monoclonal antibody.

The above described fusion protein may be prepared by a method comprising obtaining a DNA segment encoding the binding peptide or fragment thereof;

obtaining the antigenic peptide or fragment or precursor thereof and a hybridoma cell expressing a monoclonal antibody selectively binding the cell antigen;

screening a DNA library with the monoclonal antibody and selecting DNA fragments encoding peptide sequences that are selectively bound by the monoclonal antibody;

cloning into a vector the DNA segment encoding the binding peptide and one selected DNA fragment, the vector being operatively linked thereto;

transfecting host cells with the vector carrying the DNA segment and the DNA fragment and allowing the expression of a fusion protein comprising the binding peptide and the antigenic peptide;

selecting a host cell expressing the fusion protein and allowing the cell to multiply and produce cloned host cells; and culturing the cloned host cells in an expression medium and allowing the expression of the fusion protein.

The fusion protein of the invention is also provided as part of a kit for detecting the presence of neoplastic tissue from a solid tumor or metastasis thereof, the kit further comprising a first antibody or fragment thereof selectively binding to the site of the binding peptide which is absent from the antigenic peptide or fragment thereof, a second antibody or fragment thereof selectively binding to the site of the antigenic peptide or fragment or precursor thereof not present in the binding peptide and a detection means comprising an antibody-binding molecule.

A more complete appreciation of the invention and many of the attendant advantages thereof will be readily perceived as the same becomes better understood by reference to the following drawings.

BRIEF DESCRIPTION OF THE DRAWINGS

FIG. 1 depicts the competitive assay of the Peterhans et al. reference (Peterhans et al, Anal. Biochem. 163:470–475 (1987)).

FIG. 4 depicts the assay of the invention conducted in the absence (FIG. 4(a)) and in the presence (FIG. 4(b)) of analyte.

Figure 1A:
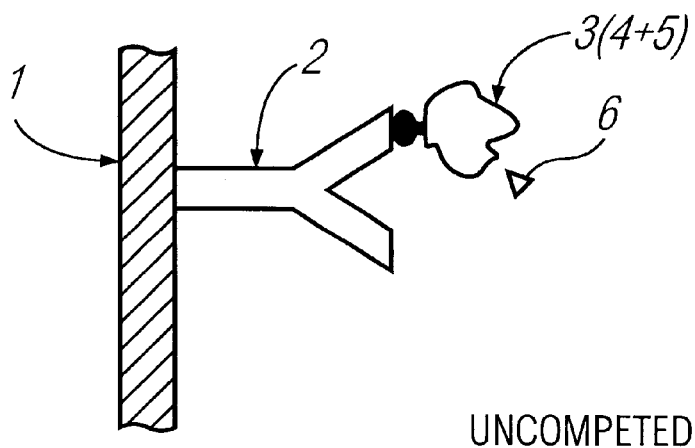
FIG. 1(a) shows the result of an uncompeted environment. The fusion protein, in the absence of an analyte, binds to the solid supported antibody.
Figure 1B:
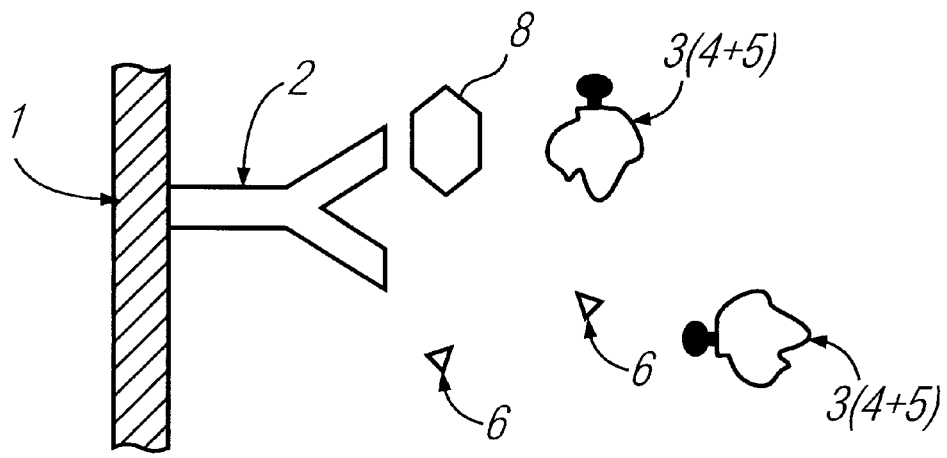
FIG. 1(b) shows the competition between the fusion protein and the analyte for the solid supported antibody.
Figure 2A:
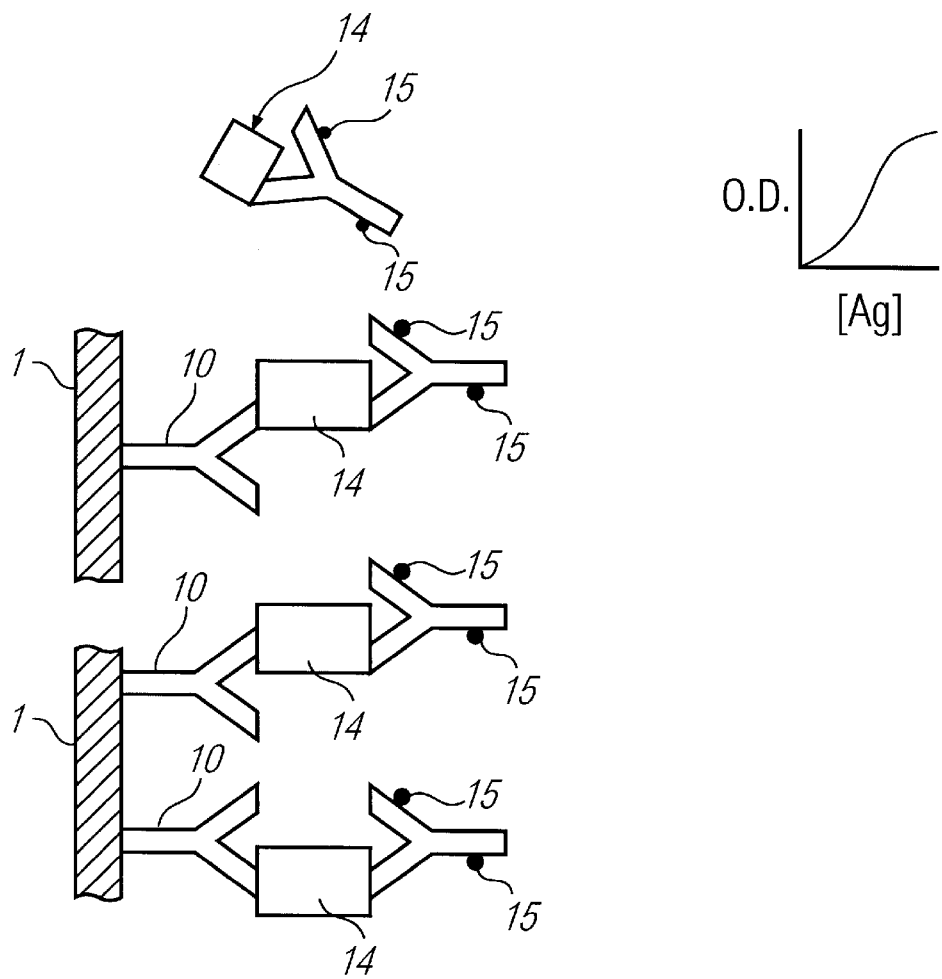
FIG. 2 shows the assay in accordance with U.S. Pat. No. 4,376,110, where one solid supported antibody competes with a free antibody for the analyte. The assay does not utilize a fusion protein, and the second antibody is shown to carry peroxidase enzyme.
Figure 2B:
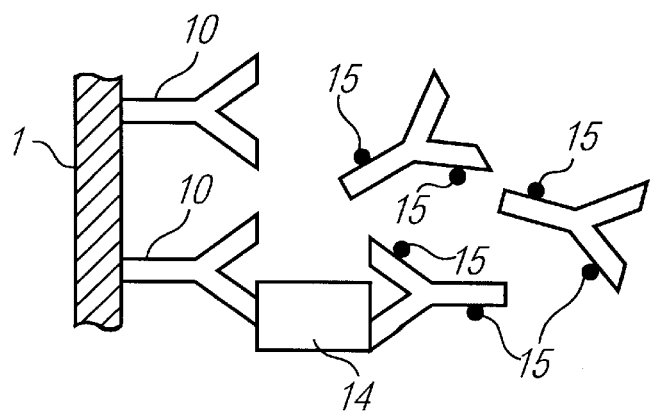
Figure 3A:
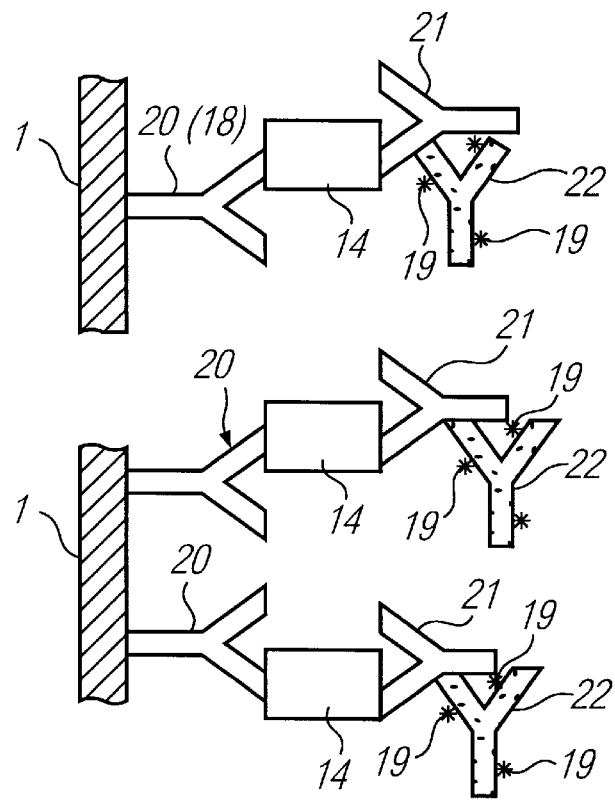
FIG. 3 shows the assay in accordance with U.S. Pat. No. 4,376,110, where the detection step is conducted with a third antibody. The assay does not utilize a fusion protein.
Figure 3B:
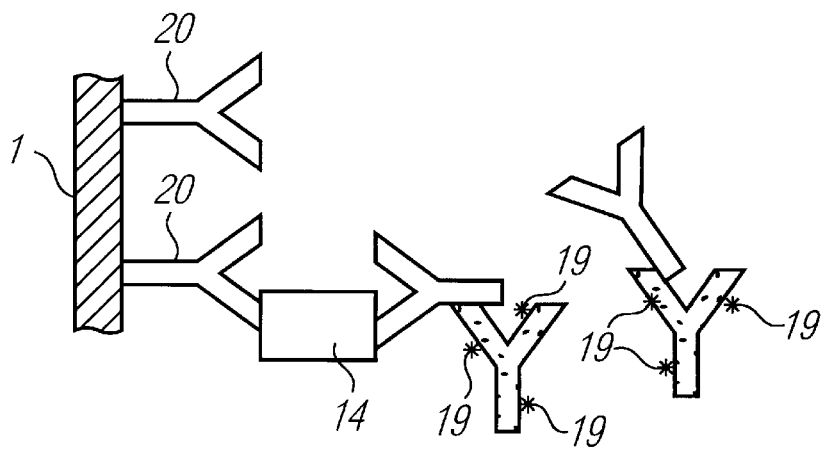
Figure 4A:
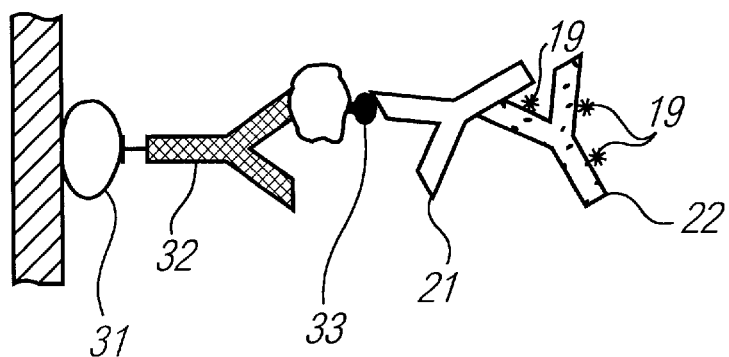
FIG. 4(a) shows the development of the assay in the presence of a sample from a normal patient.
Figure 4B:
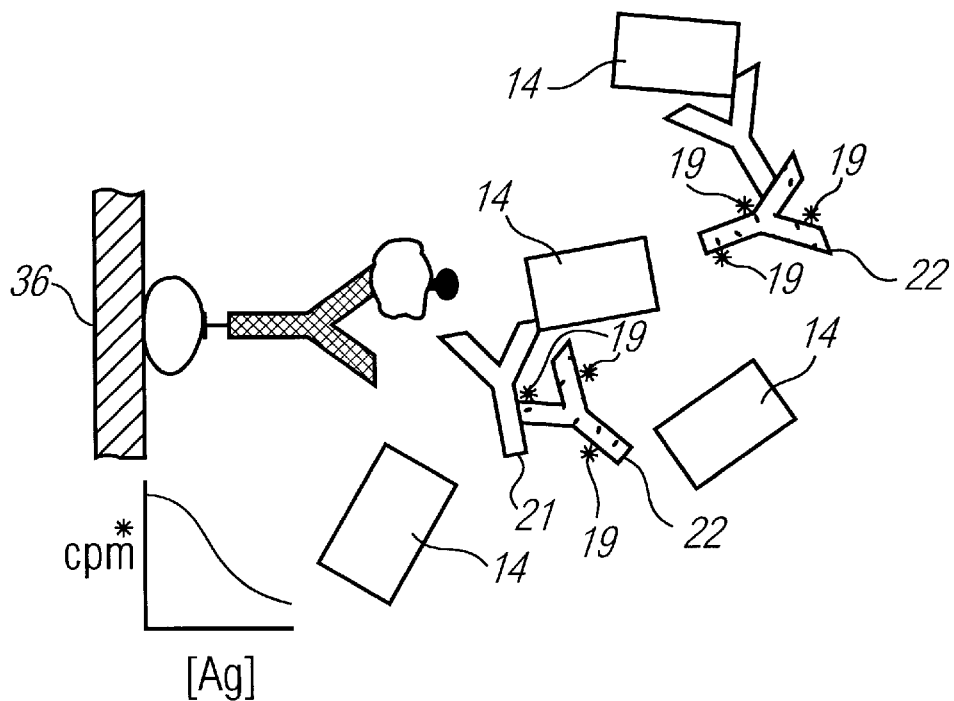
FIG. 4(b) depicts the development of the assay in the presence of a sample from a patient afflicted with breast cancer.

The invention will be better understood in reference to the following description of the preferred embodiments.

BEST MODE FOR CARRYING OUT THE INVENTION

This invention arose from a desire by the inventors to improve on known technology for detecting the presence of antigenic analytes in a biological sample. The present assay provides higher sensitivity and specificity, and greater ease, than previously known assay procedures. Of particular importance is the extremely high accuracy of the negative and positive results obtained with the present assay when applied to known populations of normal and cancer patients, where it shows a specificity and sensitivity of 100% whereas the prior art assays exhibit a high number of false positives.

In the present assay, an antibody raised against a binding peptide is attached to a solid support. Thereafter, a fusion protein of the binding peptide and an antigenic peptide containing at least one epitope in common with the analyte, is incubated with the solid support-bound antibody, and a sample to be tested is added thereto as well as an antibody that cross-reacts with the fusion protein (antigenic peptide portion) and the analyte. This permits the competition of the fusion protein and the antigenic analyte present in the sample for available binding sites on the cross-reacting antibody selectively binding the anti-antigenic peptide and their binding to it. The cross-reacting antibody is added and allowed to bind to the analyte and the antigenic peptide portion of the fusion protein, and the presence of a double antibody-fusion protein sandwich bound to a solid support is determined. The latter step can be implemented by adding a labeled antibody detecting molecule such as heterogeneic anti-constant region immunoglobulins or a fragment thereof labeled with an enzyme, a fluorescent tag and/or a radioactive atom. Other antibody binding or detecting molecules may also be utilized, such as protein A or protein G, fragments and precursors thereof, or single antibody chains, such as heavy chains.

The methodology demonstrated herein comprises a solid phase that is created on a substrate, such as microtiter wells, by coating with a polypeptide such as methylated BSA, to which an antibody having specificity for the binding peptide is bound, then adding to it a fusion protein, e.g, produced by recombinant DNA carrying bacteria, where a segment of the fusion protein comprises at least a fragment of the antigenic peptide, and another segment of the fusion protein comprises at least a fragment of the binding peptide. A biological test sample containing a peptide analyte or fragment thereof is added, and then an antibody cross-reacting with the analyte and the antigenic peptide is added in a broad range of proportions to the free antigenic segment of the fusion protein. Once the various antibody complexes have formed, a labeled antibody binding molecule such as a xenogeneic anti-constant region immunoglobulin is added with the purpose of detecting the amount of cross-reacting antibody that remains bound to the solid supported fusion protein. Optionally, the solid supported fusion protein is first separated from the medium, and the solid supported protein-antibody complex from unbound analyte-antibody complexes and the remaining biological sample.

This assay offers, among others, the following advantages. The solid phase on the microtiter well is firmly attached to the support. The antibody selectively binding the binding peptide is covalently bound to the solid phase, e.g., to the methylated BSA coated solid support. The antibody binding the binding peptide or fragment thereof participates in purifying the fusion protein, if and when added as a crude preparation. The purified fusion protein contains a purified antigenic peptide or fragment thereof that plays a key part in the assay and is, therefore, preferably purified under non-denaturing conditions. The binding peptide portion of the protein or fragment thereof is conveniently bound by the solid supported antibody on the microtiter plate for the remaining steps of the assay. The fusion protein may have its antigenic peptide substituted together with the anti-antigenic peptide antibody for assaying different analytes whereas the rest of the assay components may remain unchanged. Thus, different analytes can be tested that are associated with certain clinical conditions and be used for diagnostic purposes. The fusion protein carrying the antigenic peptide or fragment thereof may be produced in inexhaustible amounts, for instance, be recombinant technology, and the anti-antigenic peptide antibody may be prepared in inexhaustible amounts as well as a product of a hybridoma (monoclonal antibody).

The detection of the solid supported complex may be performed with antibody binding molecules with different types of conjugates providing a desired signal.

The present method may be applied to the detection of different antigens in biological fluids, such as body fluids, neoplastic or cancerous tissues, various tissue and cancer markers, and other antigenic agents which might be present in a biological sample. The biological samples may have to be treated prior to use with the present assay. When a marker, such as a neoplastic marker is found in the sample, the results may be compared with those obtained for normal tissue. The assay described herein may also be utilized for determining the origin of the tissue of the neoplastic markers. Mammalian blood or serum may be monitored for the presence of cellular antigens specifically associated with differentiated cells obtained from patients suspected of having a cancer of a particular cell type. Receptors for various determinant sites associated with normal cellular antigens may be utilized for composing the fusion protein (as the antigenic peptide).

The present assay may be applied to the measurement of levels of a specific antigenic analyte in a host's tissue suspected of having a solid primary tumor and/or metastasis thereof by comparing the results of the assay to a similar assay conducted on a sample reflecting normal levels of similar antigens in blood.

This invention provides a method for determining the presence of solid tumors and/or metastases in a mammalian host indicating not only the presence or absence of neoplastic tissue but also the nature or source of the neoplastic tissue. The method of this invention may be applied to different mammalian hosts such as research animals, domestic animals, pets and humans. The presence of elevated concentrations of associated antigens from non-circulating normal or cancer tissue may be determined, for instance, in a serum sample prepared as is known in the art. That is, cellular antigens associated with a number of different structural organs, including organs that may be encased in a facium membrane and these and other antigenic materials associated with a differentiated cell may then be monitored. Illustrative organs of interest include breast, prostate, colon, bladder, heart, kidney, lung, brain, muscle, nerves, etc.

The presence of an elevated concentration of one or more cellular antigen analytes in serum may be determined by the present assay and compared to the normal level of such cellular antigens. The cellular antigens may be free of other materials, may be a fragment of a surface antigen, may be part of a cell membrane associated with other cellular antigens or may be a cytoplasmic antigen. Particularly, the cellular antigen may be a normal antigen associated with a differentiated cell, usually a mature cell. The presence of the cellular antigen may be detected by receptors specific for one or more determinant sites. For example, some antigenic sites may be exposed while the antigen extends into the membrane or they may become exposed when the surface antigen is freed from the membrane. Other sites may not be membrane bound. Under some circumstances, it may be desirable to detect only one determinant site whereas under other circumstances two or more determinant sites, particularly determinant sites on different cellular antigens specific for the differentiated cell, may be available. In such cases it may be desirable, and even preferable, to detect two or more determinant sites on each of two or more cellular antigens specific for the differentiated cell of interest. By demonstrating that the concentration of two or more antigens specific for the differentiated cell of interest are elevated in the circulation, greater confidence in the existence of neoplastic tissue can be achieved as well as a better diagnosis of the type of tissue of origin that releases the antigen.

While any receptor or cross-reacting antibody may be employed which is specific for the determinant site(s) of interest, for the most part the receptors will be antibodies, either polyclonal or monoclonal. In addition, while any immunoglobulin may be employed, for the most part IgG will be employed, either whole antibodies or fragments thereof, e.g., $F(ab')_2$, Fab, Fd, F or heavy or light chains thereof. As indicated, while single monoclonal antibodies may be employed, sometimes mixtures of antibodies will be employed, including mixtures of monoclonal antibodies or mixtures of polyclonal antibodies. The number and type of antibodies which are employed will depend upon the number of determinant site(s) and number of different cellular antigens which are to be measured. The antibody composition is preferably free from antibodies specific for antigens other than the specified cellular antigen.

The analyte can be detected with antibodies raised against antigens present in the cell, cell membrane, or other cellular antigens of interest, and then screened against a number of different cells from other tissues. More particularly, the antibodies may be screened by combining them with cellular antigens or cell membranes from a variety of cells different from the cell of interest. In one particularly preferred embodiment, the cellular antigens and cells used for screening are bound to a support which allows the ready separation of antibodies which do not bind and those which do bind. The antibodies may then be purified by combining them with cellular antigens from cells of interest bound to a support, and further releasing the antibodies with various solutions, such as sodium isocyanate or acetic acid, at a concentration sufficient to break down the antigen-antibody complex.

The present assay is a competitive binding assay which is in general classified as heterogeneous, and may involve a separation step between free labeled materials and label bound to the solid supported double antibody-fusion protein complex. In the present assay, the support may be particles such as a beads, a container's surface such as the wall of a microtiter plate well, a tube, a chromatographic plate, and the like. Other substrates providing binding surfaces to which antibodies are bound, some of which are commercially available, may also be employed. The peptide analyte contained in the sample is allowed to compete with the solid bound fusion protein in the presence of the cross-reactive antibody or fragment thereof. One of many labels may then be attached to the latter solid supported antibody, such as radionucleides, enzymes, fluorescent molecules, and the like through antibody binding molecule. These are known in the art and need not be repeated herein.

The peptide may be any polypeptide or fragment thereof or protein comprising the antigenic peptide capable of eliciting an immunoglobulin response in a mammal. Examples thereof are β-galactosidase, chloramphenicol acetyl transferase, CII gene product of lambda phage, *E. coli* trpE gene product, alkaline phosphatase, human growth hormone or antigenic fragments or precursors thereof. However, any other antigenic peptide or active fragment or precursor thereof or protein comprising the peptide may also be utilized.

The substrate to which the anti-binding peptide antibody is attached may be any one known in the art. Preferred, however, is the one described in U.S. Pat. No. 4,572,901 to Ceriani et al, the pertinent portions thereof enabling the preparation of the substrate being incorporated herein by reference. Briefly, a proteinaceous composition is employed for modifying the binding characteristics of an article of manufacture which is capable of binding an antibody at a site other than its peptide binding site.

The antibodies raised against the antigenic peptide or active fragment thereof may be polyclonal or monoclonal antibodies and they may be bound to the solid support by methods known in the art such as the method described in U.S. Pat. No. 4,572,901. However, other methods may also be utilized. The anti-binding peptide antibody must be bound to the solid support at a site other than its binding peptide binding site in order that the solid support may not interfere with the reaction of the antibody with the binding peptide when practicing the method of the invention. The preparation of anti-antigenic peptide antibodies and anti-binding peptide antibodies is known in the art and need not be described herein in detail. By means of example, the methods disclosed in U.S. Pat. Nos. 4,229,426; 4,584,268 and 4,486,530 and Ceriani et al. (Ceriani, R .L. et al., "Surface Differentiation Antigens of Human Mammary Epithelial Cells carried on Human Milk Fat Globule" PNAS (USA) 74:582–586 (1977)), may be utilized, and the relevant parts thereof are incorporated herein by reference for enablment purposes. For the development of monoclonal antibodies standard procedures may be utilized as generally described by Kohler and Milstein (Kohler and Milstein, Nature 256:495–497(1975)), the relevant portions of which are incorporated herein by reference. The assay may be conducted with one or more monoclonal antibodies or with polyclonal antbodies.

The preparation of labeled anti-antibody immunoglobulin or similar antibody-binding molecules is also known in the art and need not be further described herein. By means of example, methods such as those described in U.S. Pat. Nos. 4,229,426; 4,486,530 and 4,632,901 and in Ceriani, et al., supra, may be utilized, the relevant parts of which are incorporated herein by reference for enablement purposes.

The preparation of fusion proteins is also known in the art and need not be fully described herein. By means of example, the techniques illustrated by Larroca et. al (Larroca, D. et al., "High Level Expression in *E. coli* of an Alternate Reading Frame of pS2 mRNA that Encodes a Mimotope of the Human Breast Epithelial Mucin Tandem Repeat", Hybridoma 11:191–201 (1991)), Handl et al, and Peterhans et al, supra and U.S. Pat. No. 4,745,055, may be utilized, the relevant portions thereof being incorporated herein by reference for enablement purposes.

Therefore, the present is an in vitro solid phase competitive assay for detecting the presence of an peptide analyte or a functional fragment or precursor thereof in a biological sample, comprising contacting a fusion protein comprising a binding peptide and an antigenic peptide or functional fragment or precursor thereof to an antibody which selectively binds to a site of the binding peptide which is absent from the antigenic peptide while the antigenic peptide portion thereof remains free, the antibody being covalently bound to a polyamino acid-coated solid support;

adding thereto a biological sample suspected of comprising a peptide analyte or functional fragment or precursor thereof;

adding thereto an antibody capable of selectively binding to the analyte peptide or fragment or precursor thereof and to a site of the antigenic peptide that is absent from the binding peptide, and allowing the antibody to bind any free peptide analyte or fragment or precursor thereof present in the sample and the free antigenic peptide portion of the solid supported fusion protein to form analyte-antibody or solid supported fusion protein-antibody complexes; and determining the amount of solid supported anti-antigenic peptide antibody present and comparing it to the amount of solid supported antibody present in a control assay, whereby when the amount of peptide analyte in the sample increases the amount of solid supported decreases.

The method of this invention may also be applied to fields other than cancer. Examples of other applications are, e.g., the measurement of hormonal levels and those of other molecules in biological samples, veterinary medicine, food and other industries, agriculture, various research fields, quality control and any other field in which immunoassays are employed.

Although preferred conditions for the practice of this invention are described hereinbelow, a skilled practitioner would know how to adapt the collective knowledge of the art for the practice of the present method as applied to different peptide analytes and the corresponding antigenic peptides.

The antibody to be bound to the solid support may be provided in solution and/or suspension at a concentration of about 0.0001 to 100 mg/ml, and more preferably about 0.0001 to 0.05 mg/ml of solution or suspension. In addition, the solution or suspension may also contain, e.g., a buffer, phosphate buffered saline +0.3% Triton X100, Tris buffered saline, and detergents, among others. The pH of the solution suspension is preferably maintained at about 6.0 to 8.0, and more preferably at about 6.80 to 7.8

The biological sample suspected of containing an antigenic analyte may be diluted and/or otherwise treated as is known in the art. By means of example, the sample may be treated as described in U.S. Pat. Nos. 4,584,268; 4,486,530 and 4,433,059. However, other treatments are also contemplated within the context of this invention which are generally known in the art.

The biological test sample is preferably treated and/or diluted so that it contains about 0.00001 to 300 mg/ml of protein, and more preferably about 0.001 to 80 mg/ml of protein. A volume of the biological sample containing about 0.0001 to 16 mg of protein, and more preferably about 0.01 to 12 mg of protein, is added to the reaction mixture already containing the above-described complex under conditions effective to promote the competition between the analyte that may be present in the biological sample and the antigenic peptide portion of the fusion protein for the subsequently added cross-reacting antibody.

The cross-reacting antibody may be added in broad proportions to the solid supported fusion protein in the reaction mixture. The exemplary disclosure shows excellent sensitivity and specificity for molar proportions of 0.3 to 1.2. However, concentrations of antibody of up to about 90% in excess of the concentration of the fusion protein to as low as about 10% of the concentration of the fusion protein in solution, and even outside of this range, may also be utilized.

About stoichiometric amounts of the antigenic peptide antibody to the free fusion protein are preferred. For the present purpose the stoichiometric point is defined as the antibody concentration at which all available antigenic sites of an antigen presented to an antibody in solution are occupied by the latter, there being no excess of antibody molecules left unbound. The stoichiometric point of an antibody or its antigen may be found as follows. Known and identical quantities of an antigen are presented to increasing concentrations of an antibody until the amount of antibody determined to be bound to the antigen reaches a plateau. This amount is considered to be the stoichiometric point. Still more preferred for quantitative results is a ratio of concentrations of antibody to fusion protein in solution slightly lower than the stoichiometric point.

The antibody may be added to the fusion protein in a given volume at a concentration of about 0.00001 to 0.06 mg/ml solution, and more preferably about 0.0003 to 0.003 mg/ml solution in phosphate buffered saline plus 0.01 to 5% bovine serum albumin at pH about 6 to 8, and more preferable about 6.8 to 7.2.

The cross-reacting antibody is thus generally added to the solid supported fusion protein and the analyte present in the reaction mixtures and is allowed to bind the antigenic portion thereof and any free analyte present in the biological sample. Preferred conditions for this step are about 4 to 40° C., more preferably about 15 to 30° C., and a pH of about 6 to 8, more preferably about 6.8 to 7.2. The incubation may be conducted to equilibrium however non-equilibrium conditions may be used. The incubations may be conducted for about several minutes to 48 hours, and more preferably about 10 to 18 hours, optionally with agitation. In one preferred embodiment of the assay of the invention, the cross-reacting antibody is labeled, such as with a radioisotope, with an enzyme, with a fluorescent label or with a peptide that selectively binds another molecule, e.g., avidine, as is known in the art.

In another embodiment, after the addition of the unlabeled cross-reacting antibody, a labeled antibody-binding molecule is added to the reaction mixture and allowed to bind the double antibody-fusion protein solid supported complex to form a labeled molecule-double antibody-fusion protein solid supported complex, prior to the detection step. The labeled antibody binding molecule may be anti-antibody immunoglobulins, protein A or G, or active fragments thereof having affinity for the constant region of an antibody, and may be added under conditions effective for the formation of a solid supported labeled antibody binding molecule/anti-antigenic peptide antibody/fusion protein/anti-binding peptide antibody complex and a free analyte or fragment thereof/anti-antigenic peptide antibody/labeled antibody binding molecule complex. The conditions may be about 4 to 40° C., and more preferably about 15 to 30° C. and a pH of about 6.0 to 8.0, and more preferably about 6.8 to 7.8.

The antibody binding molecule may be prepared by methods known in the art (e.g., Goding, T., Immunological Methods 20:241(1978) for protein A, Bjork and Kronvall J., Immunology 133:969(1984) for protein G, and U.S. Pat. Nos. 4,229,426: 4,584,268 and 4,486,530). The antibody binding molecule may carry a label such as an enzyme, a fluorescent tag or a radionucleide. Suitable labels for each category are known in the art as are the methods for attaching them to the antibody binding molecules and determine the amount of label present. The following are references describing methods for attaching such labels and are provided solely by means of example. (The and Feltkamp, Immunology 18:865–873(1970) for enzyme-linked assays, Avrameas, Immunochemistry 6:43–52(1969) for fluorescent tagging; and Greenwood et al, Biochemical J. 89:114–123 (1963) for radiolabeling).

The determination of the amount of solid supported label may be conducted by methods known in the art which are not described herein in detail. The amount of radionuclide may be determined by liquid scintillation, radioactivity counting, and other known methods. The determination of an enzyme may be conducted by adding to the solid supported label an amount of enzyme substrate and measuring the amount of the substrate converted to product or any other variable representative of the amount of enzyme present. Similarly, the amount of flourescent labeled present can be determined by measuring the amount of flourescent light at a specified wave length.

The assay requires the determination of the amount of solid supported label in the presence and absence (control) of the biological sample, for comparative purposes. The results obtained in the absence of the biological sample are taken as control and this value subtracted from the value obtained when the method is conducted in the presence of the sample.

In a particularly preferred embodiment of the invention, the anti-antigenic peptide antibody is a monoclonal antibody. In another preferred embodiment of the invention, the anti-binding peptide antibody is a monoclonal antibody. Also preferred are cocktails of monoclonal antibodies of similar but not identical specifities. In still another preferred embodiment of the invention, the solid support is coated with a ($C_1$–$C_3$)alkylated poly(amino acid) of at least about 300, more preferably at least about 3,000, and still more preferably at least about 30,000 molecular weight, that is insoluble in water at 25° C. and soluble to at least 0.01 wt. % in an aqueous solution of at least about 0.005 wt. % of a non-ionic detergent, and the anti-binding peptide antibody is bound to the poly(amino acid) via glutaraldehyde bridges. However, other polyamino acids of different characteristics may also be utilized with or without the aid of bridging molecules.

The fusion protein or functional fragment thereof is added to the solid support-bound anti-binding peptide antibody in a ratio of preferably of about 1:2,000 to 2,000:1 wt:wt, and more preferably about 1:20 to 20:1 wt:wt and allowed to incubate under conditions and for a period of time effective to form a complex between the support-bound antibody and the binding peptide portion of the fusion protein. Typically, the complex is allowed to form at a temperature of about 4 to 40° C., and more preferably at about 18 to 30° C. at a pH of about 6.0 to 8.0, and more preferably at about 6.8 to 7.8.

The antigenic analyte may comprise a tissue marker such as a cellular differentiation cell antigen or a marker for malignant cells. Examples are breast epithelial antigens, carcinoembryonic antigens, prostatic antigens, growth hormone and serum albumin, among others. However, any other antigenic cell marker may be utilized for the practice of the invention. The analyte may be a normal or malignant cell marker or antigenic fragment thereof as well.

In one aspect of the assay, the solid phase-bound complex is further separated from the remainder of the assay components before adding the anti-antigenic peptide antibody and the biological sample, before adding the labeled antibody binding molecule and before the determining step.

In a preferred embodiment, the antibody binding molecule such as anti-constant region immunologlobulins, protein A, protein G or active fragments or precursors thereof, are radiolabeled. In another preferred embodiment, the antibody binding molecule is an anti-constant region immunoglobulin, protein A, protein G, or active fragments or precursors thereof, which are enzyme labeled, and the determination of the amount of bound antibody (complex) is conducted by adding a substrate for the enzyme and determining the amount of substrate converted to product by the solid supported enzyme and comparing this value to the amount of substrate converted to product in a similar assay conducted in the absence of the biological sample. Clearly, as the amount of analyte in the sample increases, the quantity of antibody bound to the fusion protein decreases. In a further preferred embodiment of the assay, the free labeled antibody binding molecule-antibody analyte complex is separated from the solid-supported complex prior to determining the amount of label attached to the support.

Also provided is an in vitro solid phase competitive assay adapted to the detection of the presence of neoplastic tissue from a solid tumor or metastasis of a mammary organ of a mammal, that comprises contacting a fusion protein comprising a binding peptide and an antigenic peptide of an epithelial mammary cell or functional fragment or precursor thereof with an antibody which selectively binds to a site of the binding peptide which is absent from the antigenic peptide while the antigenic peptide portion thereof remains free, the antibody being covalently bound to a polyamino acid-coated solid support;

adding thereto a biological sample suspected of comprising neoplastic cells from a solid tumor or metastasis thereof or functional fragment or precursor thereof;

adding thereto an antibody capable of selectively binding to an antigen of the neoplastic cell or fragment or precursor thereof and to a site of the antigenic peptide that is absent from the binding peptide, and allowing the antibody to bind any free peptide analyte or fragment or precursor thereof present in the sample and the free antigenic peptide portion of the solid supported fusion protein to form neoplastic cell antigen-antibody or solid supported fusion protein-antibody complexes; and determining the amount of solid supported anti-antigenic peptide antibody present and comparing it to the amount of solid supported antibody present in a control assay, whereby when the amount of peptide analyte in the sample increases the amount of solid supported antibody decreases.

In general, the conditions for conducting the various steps of this assay are similar to those described above. However, these factors may have to be adapted for different applications requiring different conditions, such as pH and the like.

A variety of situations call for the serum of a host to be measured for detection of the presence of neoplastic tissue. In population screening and original diagnosis, where a host is suspected of having a neoplasm, the serum may be screened for cellular antigens of a particular tissue which is suspected of having developed the neoplasm. This test may be used in conjunction with other tests to enhance the confidence level when diagnosing, e.g., a carcinoma. Where a carcinoma has been detected and removed, the presence of residual neoplastic tissue or metastases may need to be determined. In addition, where a mass is found suggestive of a metastasis of unknown origin, the origin can be determined by employing tissue specific antibodies, that is antibodies that specifically react with a particular type of tissue. The clinical applications include the detection of the presence or absence of residual tumor masses (local or metastatic) after therapy and in the follow-up procedures to assess whether or not there is a recurrence after the neoplastic tissue has been eradicated.

When greater accuracy is needed, an antibody binding molecule may be added, which is supplied in labeled for, as described above. However, for most qualitative purposes, the utilization of a labeled anti-antigenic peptide antibody may suffice.

The antibodies and antibody binding molecules may be supplied as a lyophilized powder or in a solution that can be kept at a temperature from about below freezing to 40° C. in combination with conventional stabilizers and other additives including buffers, neutral salts, bulking agents, inert proteins, detergents such as non-ionic detergents, and other additives associated with the nature of the label, such as substrates for the enzyme label. These additives may be present in varying amounts but the following are preferred. The antibodies may be present at about 0.005 to 5 wt %, preservatives at about 0.001 to 1 wt %, neutral salts at about 0 to 15 wt %, protein at about 0 to 10 wt %, the remainder being, e.g., a bulking agent. The labeled antibody may be combined with various excipients, which serve as extenders while aiding in handling and stabilization of the labeled antibody.

The antibodies and antibody binding molecules may be provided as a kit in combination with controls to produce a standard curve. The controls will have the antigen molecule or other amino acid sequences such as those comprising epitopes and mimotopes related thereto, usually formulated with minor amounts of additives such as inert protein, non-ionic detergents, e.g. Triton X-100, buffer, preservatives, and the like. Also included may be bulking agents, e.g., mannitol. The minor additives may range from about 0.001 to 2 wt %. The antigen may be present in varying amounts to provide the desired concentration on dissolution into a prescribed volume.

The reagent antibody suspensions or solutions may contain in addition an additive such as a buffer, e.g., phosphate, Tris, barbital or the like, normally in concentrations of about 0.01 to 1 mM, and more preferably 0.05 to 0.1 mM, the concentration being effective to provide a preferred pH of about 6.5 to 9, and more preferably about 7 to 8, during the assay. Other additives which may be utilized are preservatives such as sodium azide, inert proteins such as serum albumin, sodium chloride, detergents and the like. These additives serve to preserve the proteic components of the reagents, enhance the formation of antigen-antibody complexes, prevent non-specific binding, and the like.

The present assay permits the detection of at least about 1 ng/ml to 10 mg/ml of analyte, and in some instances lower than about 1 ng/ml and even greater than about 10 mg/ml.

The fusion protein of this invention comprises a binding peptide or fragment thereof and an antigenic peptide comprising an antigen of an epithelial mammary cell or fragment or precursor thereof, the binding peptide capable of being bound by a first monoclonal antibody through a site that is absent from the antigenic peptide and lacking a site of the antigenic peptide that is capable of being bound by a second monoclonal antibody.

In a particularly preferred embodiment, the fusion protein comprises the sequence Asp Leu Arg Pro Gly Pro (SEQ. ID NO:6) or His Thr Arg Pro Ala Pro (SEQ. ID NO:41) or repeats or combinations thereof. In a still more preferred embodiment the fusion protein comprises NP5 or NP4 or fragments thereof or repeats or combinations thereof.

Peptides comprising the sequence APDTRPAPG (SEQ. ID NO:42) or fragments thereof comprising hexamers with the trimer TRP or TRP by itself or tandem repeats thereof may also be utilized for the preparation of the fusion protein, particularly as part of the antigenic peptide. The peptide comprising the hexapeptide or tripeptide sequences may be utilized as a tandem repeat comprising up to about 10,000 repeats of the basic unit, an in some instances up to about 500,000 repeats. In another embodiment, peptides comprising one or more hexapeptides or tripeptides may be operatively linked to other polypeptide sequences of related or unrelated function. The peptides comprising the hexapeptide or tripeptide may also be provided as a hybrid analogue peptide with other analogue peptides described above.

In one aspect the antigenic peptide of the fusion protein is selected form the group consisting of HMFG differentiation antigens of about 70,000, 45,000–48,000, 150,000 and 400,000 apparent molecular weights, as determined by denaturing gel electrophoresis, and binding active fragments and precursors thereof. Other antigens, however, may also be utilized to prepare the antigenic peptide. They may consist of any and all membrane molecules such as enzymes, receptors, glycoproteins, lipids and glycolipids in most tumor and tumor associated antigens, hormones, and other cell membrane molecules as well as cytoplasmic proteins such as enzymes, receptors, microtubular molecules, hormones, tumor and tumor associated antigens, glycoproteins, lipids and glycolipids and other cytoplasmic molecules.

In order to enable the practice of the assay of this invention a kit is provided for detecting the presence of an antigenic analyte. The kit may contain a fusion protein of about 6 to 12,000, and more preferably about 50 to 800 amino acids comprising an antigenic peptide or binding active fragment thereof of about 3 to 10,000 or more, and more preferably about 30 to 600 amino acids, and a binding peptide or binding active fragment thereof of about 3 to 10,000 or more, and more preferably about 5 to 600 amino acids, the binding peptide being antigenically different from the analyte;

a first antibody or binding active fragment thereof having affinity and specificity for the antigenic peptide, binding active fragment or binding active precursor thereof or protein comprising them;

a second antibody or binding active fragment thereof having affinity and specificity for the binding peptide or binding active fragment thereof, the second antibody being bound to a solid support at a site other than the binding site for the binding peptide; and optionally, an antibody binding molecule.

The fusion protein, as described above, comprises a binding peptide or binding active fragment thereof and an antigenic peptide or active fragment or precursor thereof or protein comprising them, which is antigenically different from the binding peptide. The first antibody or binding active fragment thereof, as defined above, has affinity and specificity for the antigenic binding active fragment or precursor thereof or protein comprising them. The second antibody or binding active fragment thereof also described above, has affinity and specificity for the binding peptide or a binding active fragment thereof. The second antibody is bound to a solid support at a site which is antigenically different from the binding site for the binding peptide in the antibody molecule. The characteristics of all the components for the kit have been described in this patent as have the methods for preparing them.

In a preferred embodiment of the invention the antigen selected for raising the cross-reacting antibody is the human milk fat globule (HMFG) differentiation antigens of about 70, 45–48, 150 or 400 Kdalton molecular weights, active fragments or binding active precursors thereof.

In another preferred embodiment of the invention the binding peptide is β-galactosidase or a binding fragment thereof. In another preferred embodiment the first antiantigenic peptide antibody or binding active fragment or precursor thereof or protein comprising any of them comprises a monoclonal antibody or a binding active fragment thereof. In still another preferred embodiment the second antibody raised against the antigenic peptide or active fragment thereof comprises a monoclonal antibody or binding active fragment thereof. Another preferred embodiment encompasses a first antibody raised against the antigenic peptide active fragment or precursor thereof in the form of polyclonal antibodies or binding active fragments thereof. The second antibody raised against the binding peptide or active fragment thereof may also preferably comprise polyclonal antibodies or active fragment thereof.

In a preferred embodiment of the kit of the invention, the solid support is coated with a ($C_1$–$C_3$)alkylated poly(amino acid) of at least about 30,000 Dalton molecular weight that is insoluble in water at 25° C. and soluble to at least 0.01 wt % in an aqueous solution of at least about 0.005 wt % of a non-ionic detergent, and the anti-antigenic polypeptide antibody is bound to the poly(amino acid) via glutaraldehyde bridges. The antibody-binding molecule is preferably anti-constant region immunoglobulins, protein A, protein G, and antibody binding active fragments and precursors thereof.

Also provided herein is a method of producing the fusion protein described above, comprising obtaining the antigenic peptide or fragment or precursor thereof and a hybridoma cell expressing a monoclonal antibody selectively binding the cell antigen;

screening a DNA library with the monoclonal antibody and selecting DNA fragments encoding peptide sequences that are selectively bound by the monoclonal antibody;

cloning into a vector the DNA segment encoding the binding peptide and one selected DNA fragment, the vector being operatively linked thereto;

transfecting host cells with the vector carrying the DNA segment and the DNA fragment and allowing the expression of a fusion protein comprising the binding peptide and the antigenic peptide;

selecting a host cell expressing the fusion protein and allowing the cell to grow to multiply and produce cloned host cells; and culturing the cloned host cells in an expression medium and allowing the expression of the fusion protein.

Techniques suitable for conducting every step of the above method are known in the art and need not be detailed herein (Sambrooke, et al, Molecular Cloning: A Laboratory Manual, Cold Spring Harbor) (1989); Stanley, K. K. and Luzio, I.P.,EMBO J. 3:1492–1434(1984)). Examples 6 and 7 provided below disclose the fusion proteins NP5 and NP4 and illustrate a general method for producing fusion proteins that contain a first antigenic polypeptide and at least one epitope for a single monoclonal antibody among a group of monoclonal antibodies raised against the same antigen or against the same natural polypeptide. This method is especially useful when the group of monoclonal antibodies bind to a restricted region of an antigen and it is desired to obtain an antigenic polypeptide (the second polypeptide referred to above) that binds to only one of the monoclonal antibodies. The thus constructed fusion protein is particularly useful for incorporation into a kit and/or immunoassay.

The method encompasses the screening of a cDNA or genomic expression library with a monoclonal antibody and the selection of plaques that bind the antibody with methods known in the art. Even if the DNA genomic library contains the sequence of the, e.g., natural polypeptide antigen to which the monoclonal antibody binds, there is only a 1 in 6 probability that the inserted DNAs will encode the natural polypeptide sequence given that 3 nucleotides are necessary to encode each amino acid and that there are 2 strands of DNA being constructed. There is therefore a 5/6 probability that the polypeptide antigen portion of the fusion protein encoded by the DNA insert is other than the naturally produced or antigenic epitope sequence used to raise the antibody.

These non-natural polypeptide portions of the fusion protein bind the monoclonal antibody used to select them through an amino acid region resembling the natural epitope. The rest of the polypeptide sequence is, however, antigenically different from the original antigen sequence.

The non-natural sequence containing fusion protein may be used in kits and immunoassays having greater specificity and sensitivity than assays using a fusion protein of the native antigen. Such is the case in the immunoassay discussed in example 4 below using the NP5 fusion protein and the Mc5 monoclonal antibody.

The cDNA library may be constructed with cDNA from a tissue or cell that produces a native antigen identified by the monoclonal antibody used for screening. Alternatively, it may be constructed with cDNA from a tissue or cell that does not produce that native antigen. Furthermore, the library may also be constructed with genomic DNA, since it is feasible to screen several million phage plaques with any one monoclonal antibody.

The examples, e.g., example 4 utilizing NP5 and the accompanying discussion illustrate that non-naturally occurring polypeptides and polypeptides solely sharing one epitope with an antigen may be synthesized as fusion proteins that contain antibody binding regions that resemble the natural epitope, with the rest of the polypeptide being different from that of the original antigen polypeptide against which the antibody was made.

The antigenic peptide may comprise sequences of naturally occurring as well as synthetic antigens. In a particularly preferred embodiment the antigenic peptide comprises an epitopic binding region of an antigen for a monoclonal antibody, the remainder of the antigenic peptide being the remainder sequence of the antigen or functional fragments or precursors thereof or an amino acid segment which is partially or totally antigenically different from the antigen that binds to the monoclonal antibody, and the binding peptide has at least one epitope different antigenically from the analyte and the antigenic peptide. Preferred are mimotopes of the antigenic peptide.

In order to comply with the best mode requirement, the Mc5 hybridoma cell line expressing the Mc5 monoclonal antibody has been deposited with Bernard Lerner, MD, PhD., Laboratory Director, John Muir Memorial Center, 1601 Ygnacio Valley Road, Walnut Creek, Calif. 94598. The cell line will be deposited with the ATCC in Rockville, Md. before the issuance of this patent.

Having now generally described this invention, the same will be better understood by reference to certain specific examples, which are included herein for purposes of illustration only and are not intended to be limiting of the invention or any embodiment thereof, unless so specified.

EXAMPLES

Example 1

Preparation of Methylated BSA Attached to Solid Phase Support

The methylated BSA for the solid phase in the microtiter plastic wells was prepared, used and covalently bound to the antibody having specificity for an antigenic peptide or fragment thereof as described in U.S. Pat. No. 4,572,901 to Ceriani et al.

Example 2

Preparation of Polyclonal anti-β-galactosidase Antibody

The antibody having specificity for an antigenic peptide or fragment thereof was prepared by injecting the antigenic peptide (β-galactosidase, SIGMA) to rabbits, extracting serum and absorbing it with *E. coli* strain Y1090 extracts under conditions where the microorganism does not express β-galactosidase.

Example 3

Preparation of Fusion Protein

The fusion protein was created by infecting *E. coli*, strain Y1090, with a phage population part of a cDNA library created from human breast cancer cell MCF-7, in accordance with Sambrooke et al, supra.

Bacterial phage expressing the antigenic peptide or fragments thereof as detected by monoclonal antibody Mc5 were isolated. The DNA of a lambda-phage carrying genetic information for an analyte or fragments thereof detected by Mc5 was separated by poly(ethylene glycol) precipitation, cut with restriction enzymes, and the appropriate DNA fragment carrying sequences for the analyte or fragments thereof was inserted into the circular plasmid DNA pEX2 (Stanley and Luzio, supra) at the EcoR1 restriction enzyme recognition site downstream from the lac gene. Under appropriate conditions these bacteria carrying the information for the analyte or fragments thereof produced fusion proteins comprising β-galactosidase (or fragments thereof) and the analyte (or fragments thereof). The fusion protein was concentrated in inclusion bodies in the *E. coli* bacteria. Thereafter, the inclusion bodies were separated and the fusion protein carried therein was purified as described in Example 5.

Example 4

Assay Protocol

The assays were set up as follows.
i) 50 μg of methylated BSA were dissolved in PBS+0.3% Triton X100±+0.5% sodium azide and bound to microtiter plates per well by incubation and drying overnight at 37° C. (as described in U.S. Pat. No. 4,572,901). 50 μl of buffered 0.25% glutaraldehyde were then placed in each well for 1 hr, to be followed by 50 μl of a solution containing 2 μg/ml of anti-β-galactosidase antibody. 200 μl of 0.5 mM glycine solution in PBS were added for 1 hr to block any not completely cross-linked glutaraldehyde.
ii) 0.01 to 1.0 μg of the purified fraction containing the NP5 fusion protein (SEQ. ID NO:4) dissolved in a buffer solution were added per well and let stand for 1 to 16 hrs.
iii) 30 μl of a solution containing 0.1 to 1.0 μg/ml of Mc5 monoclonal antibody (in a stoichiometric amount to the fusion protein added) were added together with 20 μl of a 1:6 dilution of patient serum in 1–30% human female serum in PBS. The Mc5 monoclonal antibody binds the about 400 Kdalton breast epithelial mucin. The mixture is let stand overnight at room temperature.
iv) The next day the monoclonal antibody was washed with PBS. Thereafter, the amount of monoclonal antibody bound to the solid phase was detected with $^{125}$I-labeled goat anti-mouse IgG by adding 200,000 to 2,000,000 cpm of the labeled immunoglobulin. The mixture allowed to stand for 1–6 hrs, the well was then washed and the amount of label counted.
v) The amount of $^{125}$I-labeled goat anti-mouse IgG bound was compared to a standard curve constructed by adding to the assay mixture increasing amounts of human milk fat globule (HMFG) diluted in 1–30% human female serum in PBS instead of patient serum.

Example 5

Preparation of Fusion Protein from Bacterial Culture 1 ml of 100 mg/ml ampicillin was added to 1000 ml of LB medium and mixed. 50 ml of inoculant culture were then added to 1000 ml of LB medium (1:20 ratio). This culture was maintained at 28–30° C. in a shaker incubator until an O.D. 600 nm =0.5 was obtained as compared to LB medium taken as blank (approximately 4 hrs). The culture was transferred to a 42° C. shaker water bath for 1 hr. and then brought back to 37° C. and incubated for 1 hr. The culture flasks were taken out and kept on ice. The contents thereof were transferred to centrifuge tubes and the tubes centrifuged at 4,500 r.p.m. for 15 minutes at 4° C. in a Sorvall GSA rotor. The supernatant was thrown away after bleach addition. The pellets were weighed and lysozyme (0.8 mg/g cells) in lysis buffer added thereto.

The suspensions were thoroughly mixed by drawing liquid up and down a pipet a number of times (Increasing viscosity signals lysis). Deoxycholate (Na salt, 4 mg/gm of cells) in lysis buffer was then added and mixed again using a pipet. The viscosity of the solution was maximal at this state. Each tube was then sonicated three times for 30 sec (30 sec. on and 30 sec. off with minimum suds formation). This solution was then centrifuged for 15-minutes at 12,000×g at 4° C. The supernate was then separated. The pellet was weighed and 9 times the volume (v/w) of lysis buffer (10 mM EDTA and 0.5% Triton X-100) was then added and mixed using a pipet. The last two steps were repeated twice and supernates II and III respectively were marked as such. The pellet was weighed and dissolved in 68 mM Tris+2% SDS+2% β-mercaptoethanol (approximately 1 gm in 90 ml) using a pipet. A 1 mM concentration of phenylmethylsulfonyl fluoride (PMSF) was then added. When the solution was completely clear, it was dialyzed against 1×PBS+0.3% Triton X-100 at room temperature.

The dialyzed preparation was run on a 7.5% stacked gel along with supernates I, II & III. A Western blot was performed to detect any protein degradation occurring during dialysis (Towbin, T. H., et al, PNAS 76:4350(1979)). The total protein concentration was estimated by the Bradford method (Bradford, M., Anal.Biochem.72:248(1976)).

Lysis Buffer
  50 mM Tris, PH=8.0 (Tris HCl)
  1 mM EDTA
  100 mM NaCl
LB Media
  Bacto-Tryptone—10 gm
  Bacto-Yeast extract—5 gm
  NaCl—10 gm
  1M Tris (pH=7.5)—10 ml
  pH to 7.5 using NaOH if necessary.
  All in 1 liter of distilled water.

Example 6

Characteristics of NP5 cDNA Insert and Fusion Protein Encoded Therein

The NP5 cDNA (SEQ. ID NO:3) insert was isolated from a λgt11 cDNA library created from the human breast cancer cell line MCF7 (Maniatis et al., supra) by screening with a monoclonal antibody mixture of Mc5, BrE1, BrE2 and BrE3 monoclonal antibodies. The fusion protein produced by bacteria infected with λgt11 containing the NP5 insert bound only the Mc5 antibody. The NP5 cDNA was transferred to the PEX2 plasmid and the β-galactosidase fusion protein was then produced by the method described in Example 3, above.

The NP5 cDNA was subcloned into pGEM3 according to standard methods (Sambrook, et al, Molecular Cloning: A Laboratory Manual, Second Edition, Cold Spring Harbor Press, New York (1989)), and sequenced by the dideoxy method using a modified T7 DNA polymerase (sequenase)

directly on the plasmid DNA using T7 or SP6 promoter sequence primers (Promega Biotec) according to the manufacturer's protocol (USB).

The DNA sequence of the coding strand was compared to sequences in GENBANK (FASTA: Intelligenetics Suite) and found to be homologous to that of human SP2 mRNA induced by estrogen (Jakowlew et al, Nucleic Acids Research 12:2861–2878(1984)). The DNA sequences are shown in Table 1 below.

The amino acid sequence of the NP5 portion of the fusion protein that bound the Mc5 monoclonal antibody was compared to known sequences in the Swiss-pro database (PFSTSCN: PCGENE) and no extended homology was found to any known polypeptide.

The amino acid sequence of the NP5 portion of the fusion protein that bound the monoclonal antibody Mc5 was compared to known sequences in Swiss-pro database (PFSTSCN: PCGENE) and no extended homology was found. Sequences compared are shown in Table 2 below.

TABLE 1

Comparison of DNA Sequence Homology Between NP5 DNA and SP2

```
NF5SP62001    5- CGCCTTTGGAGCAGAGAGGAGGCAATGGCCACCATGGAGAACAAGGTGAT
                 ::::::::::::::::::::::::::::::::::::::::::::::::
HSPS2        17- CGCCUUUGGAGCAGAGAGGAGGCAAUGGCCACCAUGGAGAACAAGGUGAU
NP5SP62001   55- CTGCGCCCTGGTCCTGGTGTCCATGCTGGCCCTCGGCACCCTGGCCGAGG
                 ::::::::::::::::::::::::::::::::::::::::::::::::::
HSPS2        67- CUGCGCCCUGGUCCUGGUGUCCAUGCUGGCCCUCGGCACCCUGGCCGAGG
NP5SP62001  105- CCCAGACAGAGACGTGTACAGTGGCCCCCCCGTGAAAGACAGAATTGTGGT
                 :::::::::::::::::::::::::::::::::::::::::::::: :::
HSPS2       117- CCCAGACAGAGACGUGUACAGUGGCCCCCCCGUGAAAGACAGAAUUGUGGU
NP5SP62001  155- TTTCCTGGTGTCACGCCCTCCCAGTGTGCAAATAAGGGCTGCTGTTTCGA
                 ::::::::::::::::::::::::::::::::::::::::::::::::::
HSPS2       167- UUUCCUGGUGUCACGCCCUCCCAGUGUGCAAAUAAGGGCUGCUGUUUCGA
NP5SP62001  205- CGACACCGTTCGTGGGGTCCCCTGGTGCTTCTATCCTAATACCATCGACG
                 ::::::::::::::::::::::::::::::::::::::::::::::::::
HSPS2       217- CGACACCGUUCGUGGGGUCCCCUGGUGCUUCUAUCCUAAUACCAUCGACG
NP5SP62001  255- TCCCTCCAGAAGTGTCTAAGGAATT (SEQ ID NO:1)
                 :::::::::::: :   :::::
HSPS2       267- UCCCUCCAGAAGAGGAGUGUGAAUU (SEQ ID NO:2)
     268 bases of a 275 nucleotide overlap are identical ( 97.5%)
```

TABLE 2

Comparison of Amino Acid Sequences of NP5 and SP2

```
                    10        20        30        40        50        60
                    |         |         |         |         |         |
NP5 cDNA   TTCCCGCCTTTGGAGCAGAGAGGAGGCAATGGCCACCATGGAGAACAAGGTGATCTGCGC

NP5 a.a.   PheProProLeuGluGlnArgGlyGlyAsnGlyHisHisGlyGluGlnGlyAspLeuArg
SP2 a.a.                                       METAlaThrMETGluAsnLysValIleCysAla
                    70        80        90       100       110       120
                    |         |         |         |         |         |
           CCTGGTCCTGGTGTCCATGCTGGCCCTCGGCACCCTGGCCGAGGCCCAGACAGAGACGTG

ProGlyProGlyValHisAlaGlyProArgHisProGlyArgGlyProAspArgAspVal
           LeuValLeuValSerMETLeuAlaLeuGlyThrLeuAlaGluAlaGlnThrGluThrCys
                   130       140       150       160       170       180
                    |         |         |         |         |         |
           TACAGTGGCCCCCCCGTGAAAGACAGAATTCTGGTTTTCCTGGTGTCACGCCCTCCCAGTG

TyrSerGlyProPro---LysThrGluLeuTrpPheSerTrpCysHisALaLeuProVal
           ThrValAlaProArgGluArgGlnAsnCysGlyPheProGlyValThrProSerGlnCys
                   190       200       210       220       230       240
                    |         |         |         |         |         |
           TGCAAATAAGGGCTGCTGTTTCGACGACACCGTTCGTGGGGTCCCCTGCTGCTTCTATCC

CysLys---GlyLeuLeuPheArgArgHisArgSerTrpGlyProLeuValLeuLeuSer
           AlaAsnLysGlyCysCysPheAspAspThrValArgGlyValProTrpCysPheTyrPro
                   250       260       270       280
                    |         |         |         |
           TAATACCATCGACGTCCCTCCAGAAGTGTCTAAGGAATTC (SEQ ID NO:3)

---TyrHisArgArgProSerArgSerVal---GlyIla (SEQ ID NO:4)
           AsnThrIleAspValProProGluValSerLysGluPhe (SEQ ID NO:5)
```

Even though the NP5 DNA (SEQ. ID NO:3) sequence is highly homologous to that of the SP2 DNA sequence, the amino acid sequence of NP5 (SEQ. ID NO:4)is different from the amino acid sequence of the SP2. The open reading frame of NP5 (SEQ. ID NO:4) starting at base 1 is different from the SP2 open reading frame starting at base 29, as shown in Table 2 above.

By epitope mapping using an Epitope Scanning Kit (Cambridge Research Biochemicals, Inc.), a series of overlapping amino acid hexamers were synthesized. The hexamers spanning the entire open reading frame of NP5 helped to determine that the only hexamer Mc5 bound to had the following amino acid sequence.

AspLeuArgProGlyPro. (SEQ. ID NO:6)

The amino acid sequence of this hexamer is only one part of the open reading frame of the NP5 region of extended homology to the amino acid sequence of the tandem repeat sequence that makes up a large part of the NPGP breast mucin (Gendler et al, J. Biol. Chem. 263: 12820 (1988). The native antigen for Mc5 is NPGP. By epitope mapping of the breast mucin tandem repeat amino acid sequence with a method similar to that described above (Gendler et al, supra) and using an Epitope Scanning Kit, it was found that Mc5 bound to only two overlapping amino acid hexamers.

AspThrArgProAlaPro, (SEQ. ID NO:7) and

ThrArgProAlaProGly. (SEQ. ID NO:8)

This binding thus occurs in the area where NP5 and the tandem repeat were found to have homology. The amino acids of the NP5 sequence that are homologous to the tandem repeat amino acids were underlined in the following portion of the NP5 sequence (SEQ. ID NO:4).

—AsPLeuArgProGlyProGly— (SEQ. ID NO:9)

This example thus illustrates that the NP5 amino acid sequence portion of a fusion protein produced by the NP5 cDNA (SEQ. ID NO:4) inserted into lambda/gt11 is novel, is synthesized in a bacteria infected with the phage carrying the cDNA sequence immediately after the β-galactosidase gene in the fusion DNA segment carried by the vector, and contains an epitope for Mc5 binding.

This NP5 fusion protein does not bind other monoclonal antibodies that bind to the tandem repeat amino acid sequence of NPGP, such as the Mc1, BrE1, BrE2 and/or BrE3 antibodies.

This example also illustrates the use of monoclonal antibodies to select a DNA fragment from a cDNA library that encodes a portion of a fusion protein that does not normally exist in nature but is produced in the bacteria as a result of being inserted after an auxiliary gene such as the β-galactosidase gene. Other auxiliary genes may be utilized instead of the β-galactosidase gene as is known in the art.

Example 7

Characteristics of NP4 cDNA Insert (SEQ. ID NO:11) and Fusion Protein Encoded Therein Another example of a fusion protein comprising the epitopic region for one monoclonal antibody of a group of monoclonal antibodies that normally bind the same molecule in nature is NP4 (SEQ. ID NO:12). The NP4 cDNA (SEQ. ID NO:11) was isolated from a lambda/gt11 cDNA library in the same manner as discussed in Example 6 for NP5 (SEQ. ID NO:3). The fusion protein produced by bacteria infected with phage DNA containing the NP4 cDNA (SEQ. ID NO:11) insert contains a short region having the following amino acid sequence.

—HisThrArgProAlaLeu— (SEQ. ID NO:10) with homology to the region of the tandem repeat.

—AspThrArgProAlaPro— (SEQ. ID NO:7) of the NPGP breast mucin that binds monoclonal antibody BrE2.

Monoclonal antibodies Mc1, Mc5, BrE1 or BrE3 bind the tandem repeat but do not bind NP4 (SEQ. ID NO:12). Furthermore, BrE3 competes with BrE2 for binding to the native NPGP breast mucin, but BrE3 does not bind the NP4 fusion protein (SEQ. ID NO:12)

An Epitope Scanning Kit was utilized to determine the epitope region on the tandem repeat amino acid sequence of the NPGP breast mucin for monoclonal antibodies BrE2 and BrE3. The results showed that both antibodies bound to the same four consecutive overlapping polypeptide hexamers with the following amino acid sequence being present in each hexamer.

ThrArgPro (SEQ. ID NO:37)

The DNA sequence and the derived amino acid sequence of NP4 cDNA are given in Table 3 below.

TABLE 3

DNA Sequence of NP4 cDNA (SEQ ID N:11) and Derived Amino Acid

```
          10        20        30        40        50        60
           |         |         |         |         |         |
GAATTCCATCACACCCGGCCGGCATTATGATTTTGTGTACTCTTGAAATGGTTATCTTTG
GluPheHisHisThrArgProAlaLeu (SEQ ID NO:12)

70        80        90       100       110       120
           |         |         |         |         |         |
TGGATGATTTTTTTTTTTAAGCTGAAACTTACCTCATGAATAACTTGATTAAAGTAGTAG 130       140       150       160       170       180
           |         |         |         |         |         |
GTGATTAAAATTTCAATAGAATCAAATGAGACAAAAATTTTAAACTGACTCATTTGAGTT
         190       200       210       220       230       240
           |         |         |         |         |         |
TCAACTTTACAGTCATTGACCATAAAGCACACTAAAAATGTAAGTTACTTTTAAATACAT 250       260
           |         |
ATAAAAATGGAATTC (SEQ ID NO:11)
```

Example 8

Materials and Assays for Epitope Mapping

The specific details of the preparation of materials, cell lines, and techniques employed were disclosed by Peterson, J. A., et al. (Peterson, J. A., et al., "Molecular Analysis of Epitope Heterogeneity of the Breast Mucin", Breast Epithelial Antigens, Ed. Ceriani, R. L., Plenum Press, NY (1991)), the relevant text of which is incorporated herein by reference.

Overlapping peptide hexamers were synthesized onto the ends of polyethylene pins using an Epitope Scanning Kit (Cambridge Research Biochemicals, Cambridge, UK), which is based on a method originally described by Geysen, H. L., et al. (Geysen, H. L., et al., "Use of Peptide Synthesis to Probe Vital Antigens for Epitopes to a Resolution of a Single Amino Acid", P.N.A.S. (USA) 81:3998–4002 (1984)). The polyethylene pins were arranged in a 8×12 configuration that fits into a 96 well microtiter dish. The pins are supplied with an alanine attached to the ends to which the amino acids are added consecutively using pentafluorophenyl active esters of fluorophenylmethyloxycarbonyl (Fmoc)-L-amino acids. Each consecutive overlapping hexamer differs from the previous one by a single amino acid and enough were synthesized to span the entire sequence of the peptide to be tested so that every combination of hexamer was present. Each monoclonal antibody was tested for binding to the synthetic peptides using an ELISA method with horse radish peroxidase-conjugated goat anti-mouse IgG (Promega, Madison, Wis.) and color development with 2,2'-azino-bis (3-ethylbenzothiazoline-6-sulfonic acid (Sigma, St. Louis, Mo.).

The hexapeptides starting with A, P, D, and T bind well to the antibodies (Hexamers 1 to 3 and 20), whereas the hexamers starting between these positions did not. The hexamers prepared are shown in Table 27 below. From the hexamer that each monoclonal antibody binds the linear amino acid sequence essential for its binding to the antigen may be deduced. For example, BrE-3 required the sequence TRP (SEQ. ID NO:37) within the hexamer. Other monoclonal antibodies required other amino acid sequences (e.g., Mc5, TRPAP (SEQ. ID NO:38); Mc1, DTR (SEQ. ID NO:40); BrE-1, DTRP (SEQ. ID NO:39)). BrE-2 also required TRP (SEQ. ID NO:37) but its different specificity for normal and tumor tissue indicates that its epitope on the native antigen is different from BrE-3.

TABLE 4

Epitope Mapping of Repeat Peptide Breast Mucin

| Hexamer | G V T S AP D T R P A P G S T A P P A H G V T S A P D T R P | |
|---|---|---|
| |        \* \*   \*       \* \*          \* \*    \* | (SEQ ID NO:13) |
| 1 | P D T R P A | (SEQ ID NO:14) |
| 2 | D T R P A P | (SEQ ID NO:15) |
| 3 | T R P A P G | (SEQ ID NO:16) |
| 4 | R P A P G S | (SEQ ID NO:17) |
| 5 | P A P G S T | (SEQ ID NO:18) |
| 6 | A P G S T A | (SEQ ID NO:19) |
| 7 | P G S T A P | (SEQ ID NO:20) |
| 8 | G S T A P P | (SEQ ID NO:21) |
| 9 | S T A P P A | (SEQ ID NO:22) |
| 10 | T A P P A H | (SEQ ID NO:23) |
| 11 | A P P A H G | (SEQ ID NO:24) |
| 12 | P P A H G V | (SEQ ID NO:25) |
| 13 | P A H G V T | (SEQ ID NO:26) |
| 14 | A H G V T S | (SEQ ID NO:27) |
| 15 | H G V T S A | (SEQ ID NO:28) |
| 16 | G V T S A P | (SEQ ID NO:29) |
| 17 | V T S A P D | (SEQ ID NO:30) |
| 18 | T S A P D T | (SEQ ID NO:31) |
| 19 | S A P D T R | (SEQ ID NO:32) |
| 20 | A P D T R P | (SEQ ID NO:33) |

Example 9

Epitope Mapping

Five different monoclonal antibodies (Mc1, Mc5, BrE1, BrE2 and BrE3), were prepared using the human milk fat globule (HMFG) for immunization. All identified epitopes on the highly glycosylated large molecular weight breast mucin. By immunohistochemistry they appeared to recognize different epitopes since each had different tissue and tumor specificities (Peterson, J. A., et al., "Biochemical and Histological Characterization of Antigens Preferentially Expressed on the Surface and Cytoplasm of Breast Carcinomas Cells Identified by Monoclonal Antibodies Against the Human Milk Fat Globule", Hybridoma 9:221–235 (1990)). Each monoclonal antibody bound to a different spectrum of normal tissues and their specificities for different carcinomas were different. BrE2 and BrE3, however, were quite similar. In addition, by screening breast λgtII cDNA expression libraries with some of these monoclonal antibodies, cDNA clones were isolated that produced fusion proteins that bound all of them, while other cDNA clones bound just some (Larroca, D., et al., "High Level Expression in *E. Coli* of an Alternate Reading Frame of pS2 mRNA that Encodes a Mimotope of Human Breast Epithelial Mucin Tandem Repeat" Hybridoma 11(2):191–201 (1992)).

This binding to the fusion proteins indicated that the epitopes for these 5 monoclonal antibodies included the polypeptide portion of this glycoprotein. To confirm this the binding of these monoclonal antibodies to two synthetic polypeptide 20-mers (PDTRPAPGSTAPPAHGVTSA (SEQ. ID NO:34) and APPAHGVTSAPDTRPAPGST (SEQ. ID NO:35)) that spanned the tandem repeat consensus sequence was tested (Gendler, S. J., et al., "Cloning of Partial cDNA Encoding Differentiation and Tumor-Associated Mucin Glycoproteins Expressed by Human Mammary Epithelium", P.N.A.S. (USA) 84:6060–6064 (1987); Siddiqui, J., et al., "Isolation and Sequencing of a cDNA Coding for the HUman DF3 Breast Carcinoma-Associated Antigen", P.N.A.S. (USA) 85:2320–2323 (1988)).

One was started at the beginning of the published 20 amino acid repeat (Gendler, S. J., et al. (1987), supra) unit, and the other was started in the middle. All five monoclonal antibodies bound to both synthetic peptides, as did DF3, a monoclonal antibody against breast carcinoma cells produced by others (Hull, S. R., et al., "Oligosaccharide Diferences in the DF3 Sialomucin Antigen from Normal Human Milk and the BT-20 Human Breast Carcinoma Cell Line", Cancer Comm. 1:261–267 (1989)). Three other monoclonal antibodies (Ceriani, R. L., et al., "Characterization of Cell Surface Antigens of Human Mammary Epithelial Cells with Monoclonal Antibodies Prepared Against Human Milk Fat Globule", Somat. Cell Genet. 9:415–427 (1982); Peterson, J. A., et al., "Biochemical and Histological Characterization of Antigens Preferentially Expressed on the Surface and Cytoplasm of Breast Carcinoma Cells Identified by Monoclonal Antibodies Against the Human Milk Fat Globule", Hybridoma 9:221–235 (1990)) against other components of the HMFG that do not cross-react with the breast mucin, Mc13, against a 70 KDa glycoprotein, and Mc3 and Mc8, against a 46 KDa glycoprotein do not bind to these synthetic peptides (data not shown).

Example 10

Assay of Invention Shows 100% Sensitivity and Specificity over Broad Antibody: Antigen Proportion (Samples with Known Amounts of Antigen)

The assay was conducted as described in Example 4, except that different concentrations of the non-penetrating glycoprotein (NPGP) were substituted for patient's samples. NPGP is the native antigen and breast cancer marker, which the antibody used detects. The NPGP samples were diluted in human serum obtained from a normal woman, and prepared to contain analyte concentrations of 0.01 µg/ml, 0.03 µg/ml, 0.1 µg/ml and 1.0 µg/ml. The NPGP was prepared in accordance with Ceriani et al (Ceriani, R. L., et al, Breast Cancer Res. and Treatment 24:103(1992)).

The assay was also conducted at different monoclonal antibody Mc5 concentrations encompassing values below and above the stoichiometric point with respect to the fusion protein. The assay was conducted at antibody concentrations of 0.3 µg/ml, 0.6 µg/ml, 1.2 µg/ml, 1.8 µg/ml and 2.4 µg/ml. The fusion protein was added at 1.2 µg/ml prior to the addition of the antibody. The results obtained are shown in Table 5 below.

TABLE 5

Assay of Invention Conducted over Broad Antibody-antigen Proportion with Known Amounts of NPGP Antigen in Samples

| Antigen | Concentration of Analyte (µg/ml) | Monclonal Antibody Mc5 | | | | |
|---|---|---|---|---|---|---|
| | | 0.3 | 0.6 | 1.2 | 1.8 | 2.4 |
| NPGP | 0.01 | – | – | – | – | – |
| NPGP | 0.03 | – | – | – | – | – |
| NPGP | 0.1 | – | – | – | – | – |
| NPGP | 1.0 | + | + | + | + | + |
| Fusion protein | (µg/ml) | 1.2 | 1.2 | 1.2 | 1.2 | 1.2 |

These results show that at low concentrations of the analyte (below the cut-off point), the assay yields negative results at all concentrations of antibody tested. As the concentration of antigen exceeds the cut-off value taken as the amount above which there is an indication that carcinoma cells are present in a patient, the assay yields positive results at all concentrations of antibody used in the assay. Utilizing samples of known concentrations, it has been clearly shown that the assay exhibits 100% sensitivity, and that it yields such results over a broad range of antibody-:antigen concentrations. These results also show that all samples of analyte (NPGP) of concentrations known to be above the cut-off point of 0.9 µg/ml are detected by the assay of the invention as positives over a wide range of cross-reacting antibody concentrations and proportions to the fusion protein. A probability of 0.05 or below is considered to be statistically significant. In this case p=0 indicating that there is a complete identification of a sample as positive by this test once levels surpass levels of the analyte found in normal women.

Example 11

Assay of Invention Shows 100% Sensitivity and Specificity over Broad Antibody: Antigen Concentrations (Normal and Breast Cancer Patients)

The assay was conducted as described in Example 4 above with two normal samples (N50 and N76) and 3 samples of breast cancer patients (Z153, W68 and Davis-10). The concentration of the antibody was as in Example 8 and the results of this test are shown in Table 6 below.

TABLE 6

Assay of Invention Conducted over Broad
Antibody:antigen Proportion with Samples from
Known Normal and Breast Cancer Patients

| Patient | Patient Status | Monoclonal Antibody Mc5 (μg/ml) | | | | |
|---|---|---|---|---|---|---|
| | | 0.3 | 0.6 | 1.2 | 1.8 | 2.4 |
| N50 | Normal | − | − | − | − | − |
| N76 | Normal | − | − | − | − | − |
| Z153 | Breast Cancer | + | + | + | + | + |
| W68 | Breast Cancer | + | + | + | + | + |
| Davis-10 | Breast Cancer | + | + | + | + | + |
| Fusion Protein | (μg/ml) | 1.2 | 1.2 | 1.2 | 1.2 | 1.2 |

The results shown in Table 6 above clearly indicate that the assay exhibits 100% sensitivity and specificity. The assay of this invention recognizes normal and cancer samples as such 100% of the time at all concentrations of antibody and fusion protein tested. It is clearly shown in Table 5 that the sera from breast cancer patients are detected as positive by the assay while those of normal women are detected as negative. These determinations were performed with a wide range of antibody concentration in the assay mix, above and below the stoichiometric point determined for this fusion protein and antibody.

Example 12

Assay of Invention Conducted with Diluted Breast Cancer Patient's Samples

To further test the sensitivity of the assay at decreasing analyte concentrations, serial dilutions of the serum of a woman with breast cancer were performed by adding normal woman serum to equalize the protein concentrations in all samples. The W68 cancer sample and 1:2, 1:4 and 1:8 dilutions thereof were tested. The results are shown in Table 7 below.

TABLE 7

Assay of Invention Conducted with Diluted Samples

| Patient | Dilution | Condition | Monoclonal Antibody Mc5 (μg/ml) | | | | |
|---|---|---|---|---|---|---|---|
| | | | 0.3 | 0.6 | 1.2 | 1.8 | 2.4 |
| W68 | 1/2 | Breast Cancer | + | + | + | − | − |
| W68 | 1/4 | Breast Cancer | + | + | + | − | − |
| W68 | 1/8 | Breast Cancer | + | + | − | − | − |
| Fusion Protein | | (μg/ml) | 1.2 | 1.2 | 1.2 | 1.2 | 1.2 |

From the results shown in the table, it can be seen that the lower analyte concentrations originated by dilution could still be detected when the assay was run employing antibody concentrations at the level of or below the stoichiometric point, that was determined in this case to be at approximately 1.1 μg/ml of antibody. When the samples having the lowest analyte concentrations (⅛ dilution) were tested with concentrations below the stoichiometric point, the assay showed to be more sensitive than when employing antibody concentrations above the stoichiometric point. This is the area of Table 7 above to the left of the middle column. The concentration of antibody at 0.6 μg/ml lies approximately in the 50% range of the stoichiometric point. This effect can be related to, and explained by, the conditions required by the Ekins model (in Monoclonal Antibodies and Developements in Immunoassays", Albertini et al., eds., Elsevier, N.Y. (1981)). The Elkins model provides support for the fact that maximal sensitivity is achieved at an antibody concentration around 50% of the stoichiometric point. As the concentration of antibody increases above the 50% range, the sensitivity of the assay diminishes, and is evidenced first at the most dilute levels of analyte. Thus, maximum sensitivity is needed at the highest dilution of the analyte, e.g., Table 5, last line, shown above, and dilutions of the antibody below maximal binding are more sensitive to the presence of analyte. It is at these low analyte concentrations that the assay is most sensitive at very low concentrations of antibody.

Example 13

Use of Different Polypeptides for Coating Solid Substrate

The following experiments were conducted to compare the results obtained with the present assay using methylated serum albumin (U.S. Pat. No. 4,572,901) and other means of covalently attaching an antibody to a solid support.

Methylated serum albumin as well as other polypeptides were used to covalently bind the antibody to the solid phase, and the binding was also conducted without polypeptides, and with other modifications affecting the binding of the antibody to the solid support, such as glutaraldehyde.

As applied herein, the assay detects breast epithelial mucin antigen present in breast cancer patients' serum and in the human milk fat globule. The serum samples were obtained from the following subjects.

a) Two normal female subjects.

b) Four female breast cancer patients at a late high tumor load stage (having medium and high levels of the mucin).

The assay of the invention was then conducted with the antibody (anti-β-galactosidase) bound to the solid phase in various fashions, and the results were then compared.

Example 14

Assay of the Invention with Methylated Serum Albumin- and Glutaraldehyde-coated substrate A solid phase was created as follows. The wells in a microtiter plate were coated with methylated serum albumin to covalently link the albumin to the solid support. Thereafter, rabbit anti-β-galactosidase antibody was covalently bound to the methylated serum albumin through a glutaraldehyde linkage in accordance with U.S. Pat. No. 4,572,901 to Ceriani et al. A solid phase was thus created comprising the anti-β-galactosidase antibody covalently bound to methylated serum albumin, that in turn was bound to the solid phase. This solid supported antibody selectively bound the β-galactosidase portion of the fusion protein carrying a modified breast epithelial mucin peptide and, thus, it purified the fusion protein when added as from a crude preparation. After the β-galactosidase portion of the fusion protein was bound to the antibody fixed onto the solid phase, the modified mucin peptide portion of the fusion protein remained free to participate in the competitive part of the assay of the invention.

The competitive part of the assay was conducted as follows. An anti-mucin antibody was added in stoichiometric amounts with respect to the solid supported fusion protein and a patient's serum comprising the analyte to be measured was then added. The analyte shared amino acid sequences with the modified mucin portion of the solid supported fusion protein and can, therefore, compete for the anti-mucin antibody and form an antibody-antigen complex. Labeled goat-anti-mouse antibody was then added to detect the amount of goat-anti-mouse bound to the solid phase, as shown in the following scheme.

Solid phase M-BSA>>rabbit anti-β-galactosidase>>fusion protein>>
>>MoAb>>$^{126}$I-labeled goat anti-mouse Ab To obtain quantitative values, a known amount of mucin was added to control samples and allowed to compete for the anti-mucin antibody with the modified mucin portion of the fusion protein on the solid phase. The amount of anti-mucin antibody bound to the solid supported fusion protein was then detected by addition of labeled secondary goat-anti-mouse antibody and the results obtained were compared to those obtained for the serum to determine the values of the analyte in serum.

Example 15

Application of Various Treatments to the Solid Substrate

The effectiveness of the assay of the invention when different means of attaching an antibody to the solid support was ascertained by treating microtiter plates as follows to prepare the solid phase to which the anti-β-galactosidase antibody was attached.

(A) Dissolved anti-β-galactosidase was presented directly (without protein coating) to the wells in the microtiter plate at pH 8.4 and allowed to stand overnight to permit attachment. The solid phase was thus ready to be used for the purification step.

(B) Same as A but conducted at pH 7.0.

(C) 0.01% polylysine (Sigma) dissolved in water was presented directly to the wells in a microtiter plate and allowed to stand for 1 hour to permit attachment. The polylysine coated substrate was then added anti-β-galactosidase dissolved in phosphate buffered saline 0.02 M, pH 7.0 (PBS), 0.02 M, Triton X-100 0.3% and 0.05% Na azide, and was allowed to stand overnight to permit attachment. The solid phase was thus ready for the purification step.

(D) 0.1% polylysine dissolved in water was presented directly to the wells in a microtiter well and allowed to stand for 1 hour to permit attachment. The polylysine coated substrate was then added a solution of 0.25% glutaraldehyde in PBS, allowed to stand for 1 hour to permit attachment, and washed twice with PBS and 0.05% azide. Anti-β-galactosidase was then added and allowed to stand overnight to permit attachment. In addition, a solution of 0.5% glycine was then added and allowed to stand for 1 hour to block unconjugated glutaraldehyde, and washed with PBS plus 0.05% Na azide. The solid phase was thus ready for the purification step.

(E) A solution of 0.25% glutaraldehyde was presented directly to the wells in a microtiter plate, and allowed to stand for 1 hour to permit attachment and washed twice in PBS and 0.05% azide. Anti-β-galactosidase was then added and allowed to stand overnight to permit attachment and then washed once with PBS and 0.05% azide, and a solution of 0.5% glycine was added for 1 hour, and washed with PBS plus 0.05% Na azide. The solid phase was thus ready for the purification step.

Example 16

Results

The analyte (the breast epithelial mucin) present in the sera of 4 patients with breast cancer and the values obtained were compared to those from the sera of 2 normal women. The results obtained by conducting the assay for the different sera in accordance with the different treatments outlined above are shown in Table 7 below.

TABLE 7

Comparative Results

| Serum Origin | Procedure | | | | | |
|---|---|---|---|---|---|---|
| | A | B | C | D | E | Methy'd Alb./ Glutarald. |
| Normal Subject (1) | − | − | − | − | − | − |
| Normal Subject (2) | − | − | − | − | − | − |
| Breast Cancer Patient (1) | + | − | + | + | + | + |
| Breast Cancer Patient (2) | + | + | + | + | + | + |
| Breast Cancer Patient (3) | + | + | + | + | + | + |
| Breast Cancer Patient (4) | + | + | + | + | + | + |

All tested means of attaching the anti-β-galactosidase antibody to the solid support yielded similarly excellent results to those obtained with methylated albumin/glutaraldehyde as described in U.S. Pat. No. 4,572,941, with the exception of method B (see, Table above). The anti-β-galactosidase antibody bound via glutaraldehyde to methylated-BSA as described in U.S. Pat. No. 4,572,941 clearly showed the highest overall binding to the solid substrate.

The assay of the invention yields correct results (positives and negatives) and may be successfully conducted with a polypeptide other than methylated albumin, such as polylysine, coating the solid substrate. Moreover, the antibody may be directly attached to the solid substrate by direct binding to the microtiter plate at a high pH (pH 8.0 or higher) in the absence of a polypeptide layer and/or glutaraldehyde. The antibody may also be attached to the solid substrate through a polypeptide with or without glutaraldehyde or it may be attached directly through a bridge, such as glutaraldehyde. Accordingly, good diagnostic results are obtained whether the present method is practiced by coating the solid support with different polypeptides, with or without glutaraldehyde or without a polypeptide coating at all. The only exception is when the antibody is attached to the substrate at a pH 7 or lower.

When methylated-BSA was used to coat the solid support, both for the standard curve and for the individual tests, the amount of radioactivity bound thereto were the highest compared to all the other means of treating the solid support. This indicates that a larger amount of the anti-β-galactosidase antibody was selectively fixed to the solid phase, which in turn selectively increased the amount of bound fusion protein, which in turn increased the amount of bound anti-mucin antibody, resulting in a total selective increase of radioactivity in the methylated-BSA coating test. Higher amounts of counts facilitate the selective identification of diseased and normal samples using a standard curve

Example 17

Effect of Rinsing after Various Steps of the Assay

This experiment was performed to assess the effect on the assay of the invention of rinsing performed after different steps. As applied herein, the assay detects the breast epithelial mucin present in breast cancer patients' serum and also present in the human milk fat globule. The serum samples were obtained from a) One normal female subject.
b) Two female breast cancer patients at a late high tumor load stage (having high or very high value of the mucin).
c) One breast cancer patient whose breast tumor was removed and who remained healthy and without evidence of disease.

The assay of the invention was conducted as follows. A solid phase was first created to purify a fusion protein comprising a modified mucin and a binding peptide as follows. Wells in a microtiter plate were coated with methylated bovine serum albumin to covalently link the albumin to the solid support. Thereafter, rabbit anti-β-galactosidase antibody was then covalently bound to the methylated serum albumin through a glutaraldehyde linkage arm in accordance with U.S. Pat. No. 4,572,901 to Ceriani et al. Thus, a purifying solid phase was created comprising the anti-β-galactosidase antibody covalently bound to methylated serum albumin, that in turn was bound to the solid phase. This solid supported antibody selectively bound the fusion protein carrying the antigenic peptide comprising a modified epitope of the breast epithelial mucin and, thus, purified it from a crude preparation. After the β-galactosidase portion of the fusion protein is bound to the anti-β-galactosidase antibody, the antigenic peptide remains free to participate in the competitive assay of the invention. The competition part of the assay was conducted as follows. A specific anti-mucin antibody was added in stoichiometric amounts with respect to the solid supported fusion protein. A patient's serum comprising the analyte to be measured was then added. The analyte shares amino acid sequences with the modified antigenic peptide (NPGP or mucin) portion of the solid supported fusion protein and therefore can compete for the anti-mucin antibody and forms an antibody-antigen complex. A labeled goat-anti-mouse antibody was then added to detect the amount of goat-anti-mouse bound to the solid phase.

To obtain quantitative values, a known amount of mucin was added to control samples and allowed to compete for the anti-mucin antibody with the modified mucin portion of the fusion protein on the solid phase. The amount of anti-mucin antibody bound to the solid supported fusion protein was then detected by addition of labeled secondary goat-anti-mouse and the results obtained were compared to those obtained for the serum to determine the values of the analyte in serum.

To test the effect of omitting different washes on the ability of the serum assay to detect breast cancer samples, the assay was conducted with various aliquots of the same sera as follows.

A. With Three Washes

Solid phase/M-BSA>>rabbit anti-β-galactosidase>>fusion protein>>Moab>>
wash
$^{125}$I-labeled goat anti-mouse Ab B. With Two Washes

Solid phase/M-BSA>>rabbit anti-β-galactosidase>>fusion protein>>Moab>>
wash
$^{125}$I-labeled goat anti-mouse Ab C. With Two Washes

Solid phase/M-BSA>>rabbit anti-β-galactosidase>>fusion protein>>Moab>>
wash $^{125}$I-labeled goat anti-mouse Ab D. With One Wash
Solid phase/M-BSA>>rabbit anti-β-galactosidase>>fusion protein>>Moab>>
wash

-continued $^{125}$I-labeled goat anti-mouse Ab

The washes were only performed at the point(s) indicated as follows.

wash

The levels of the analyte (the breast epithelial mucin) were tested in the sera of two patients with advanced breast cancer and the values obtained were compared to those from the sera of a normal woman and a woman whose breast cancer was removed and who remained tumor free. The results obtained from the assay for the different sera are identified as follows.

A—3 washes

B—2 washes (after fusion protein)

C—2 washes (after monoclonal antibody)

D—1 wash

The results are shown in the Table 8 below.

TABLE 8

| | Results | | | |
|---|---|---|---|---|
| | Washes | | | |
| Sample | A* | B* | C* | D* |
| Active breast cancer | + | + | + | + |
| Active breast cancer | + | + | + | + |
| Patient treated by surgery, now without breast cancer | – | – | – | – |
| Normal woman | – | – | – | – |

*Cut-off value: 0.98 µg/ml.

The above serum values clearly show that the present assay provides substantially the same results whether or not washing steps are conducted during the assay. The presence or absence of washing does not appear to alter the results obtained with the assay of the invention. All samples that were positive with washes after every step (A: three washes) were also positive if either one (B, C) or the two washes (D) other than the radiolabel separation wash were omitted (restricted washes B, C and D). Also, all samples that were negative with all three washes (A) were also negative if either one (B or C) or all washes (D) other than the radiolabel separation wash were omitted.

These results indicate that the serum assay of the invention yields similar results for a given sample whether washing is performed after every step (A) or it is omitted after placing the fusion protein on the plate (B), omitted after placing the monoclonal BrE-3 on the plate (C), or omitted after sequentially placing the fusion protein and the monoclonal antibody BrE-3 on the plate (D). All results obtained for a given sample were similar.

Example 18

Comparison of Assay of Invention with U.S. Pat. No. 4,376,110 Assay

The following is a side-by-side comparison of the assay of the invention and the assay of U.S. Pat. No. 4,376,110. These experiments were performed to assess the relative characteristics of the assay of the invention and a sandwich assay in accordance with U.S. Pat. No. 4,376,110 a kit by Centocor, Malvem, Pa. Both assays were applied to the detection of breast epithelial mucin present in the serum of breast cancer patients and in the human milk fat globule. However, both assays may be applied to the detection of other antigens.

Serum samples were obtained from the following patients and were used for the assays of the invention and in accordance with U.S. Pat. No. '110.

a) Normal female subjects.

b) Female breast cancer patients at a late high tumor load stage.

The latter group (cancer patients) is expected to have a high or very high content of the mucin in serum.

The negative and positive results were obtained by comparing the values obtained for each sample with established cut-off values for each assay (all samples), and the sensitivity and specificity of the assays calculated as described in Clinical Diagnosis and Management: Laboratory Methods, Henry J. B., Ed., vol I, p. 528, Ch. 16, p.8, W. B. Saunders & Co. Publishers (1979).

Example 19

Assay of the Invention

The assay of the invention was conducted as described in the above-identified application as follows. A solid phase was created before adding the fusion protein comprising a modified mucin and a binding peptide as follows. Wells in a microtiter plate were coated with methylated bovine serum albumin to covalently link the albumin to the solid support. Thereafter, rabbit anti-β-galactosidase antibody was then covalently bound to the methylated serum albumin through a glutaraldehyde linkage arm in accordance with U.S. Pat. No. 4,572,901 to Ceriani et al. Thus, a purifying solid phase was created comprising the anti-β-galactosidase antibody covalently bound to methylated serum albumin, that in turn was bound to the solid phase. This solid supported antibody selectively bound the fusion protein carrying the antigenic peptide comprising a modified epitope of the breast epithelial mucin and, thus, purified it from a crude preparation. After the β-galactosidase portion of the fusion protein is bound to the anti-β-galactosidase antibody, the antigenic peptide remains free to participate in the competitive assay of the invention. The competition part of the assay was conducted as follows. A specific anti-mucin antibody was added in stoichiometric amounts with respect to the solid supported fusion protein. A patient's serum comprising the analyte to be measured was then added. The analyte shares amino acid sequences with the modified mucin portion of the solid supported fusion protein and therefore can compete for the anti-mucin antibody and forms an antibody-antigen complex. A labeled anti-rabbit-anti-mucin antibody was then added to detect the amount of rabbit-anti-mucin bound to the solid phase.

To obtain quantitative values, a known amount of mucin was added to control samples and allowed to compete for the anti-mucin antibody with the modified mucin portion of the fusion protein on the solid phase. The amount of anti-mucin antibody bound to the solid supported fusion protein was then detected by addition of labeled secondary anti-rabbit-antibody and the results obtained were compared to those obtained for the serum to determine the values of the analyte in serum.

Example 20

Assay Conducted in Accordance with U.S. Pat. No. 4,376,110

The assay in accordance with U.S. Pat. No. 4,376,110 was conducted as described in the specifications provided with the kit (CENTOCOR).

Example 21

Results

Different levels of the analyte, the breast epithelial mucin, were measured in the serum of patients with advanced breast cancer and compared to the values measured in the serum of normal women.

The groups compared were normal female serum vs. patients with a late stage of breast cancer. For these patients, the values of the mucin in serum are elevated due to the high tumor load and the existence of large amounts of tumor cells producing and releasing the mucin into the serum.

40 serum samples of normal subjects and 25 serum samples of late stage breast cancer patients were tested. The positive and negative values obtained with both assays were tabulated in accordance with established cut-off values and are shown in Table 8 below.

TABLE 9

Comparison of Assay of Invention with U.S. Pat. No. 4,376,110

| | SAMPLE | Assay of the Invention* µg/ml | Assay according to U.S. Pat. No. 436110** µ/ml |
|---|---|---|---|
| | | NORMAL SERA | |
| 1. | N031 | – | – |
| 2. | N032 | – | – |
| 3. | N033 | – | + |
| 4. | N034 | – | – |
| 5. | N035 | – | – |
| 6. | N036 | – | – |
| 7. | N037 | – | – |
| 8. | N040 | – | – |
| 9. | N044 | – | – |
| 10. | N045 | – | – |
| 11. | N046 | – | – |
| 12. | N047 | – | – |
| 13. | N048 | – | – |
| 14. | N049 | – | – |
| 15. | N050 | – | – |
| 16. | N051 | – | – |
| 17. | N052 | – | – |
| 18. | N053 | – | – |
| 19. | N054 | – | – |
| 20. | N055 | – | + |
| 21. | N056 | – | – |
| 22. | N057 | – | – |
| 23. | N058 | – | – |
| 24. | N059 | – | – |
| 25. | N060 | – | – |
| 26. | N061 | – | – |
| 27. | N062 | – | – |
| 28. | N063 | – | – |

TABLE 9-continued

Comparison of Assay of Invention with U.S. Pat. No. 4,376,110

| | SAMPLE | Assay of the Invention* µg/ml | Assay according to U.S. Pat. No. 436110** µ/ml |
|---|---|---|---|
| 29. | N064 | – | – |
| 30. | N065 | – | – |
| 31. | N066 | – | – |
| 32. | N067 | – | – |
| 33. | N068 | – | – |
| 34. | N069 | – | – |
| 35. | N071 | – | – |
| 36. | N072 | – | – |
| 37. | N073 | – | – |
| 38. | N074 | – | – |
| 39. | N075 | – | – |
| 40. | N076 | – | – |
| | | ACTIVE BREAST CANCER | |
| 41. | W85 | + | + |
| 42. | W001 | + | + |
| 43. | W001 | + | + |
| 44. | W006 | + | + |
| 45. | W29 | + | + |
| 46. | W010 | + | + |
| 47. | W019 | + | + |
| 48. | W024 | + | + |
| 49. | W024 | + | + |
| 50. | W024 | + | + |
| 51. | W028 | + | + |
| 52. | W029 | + | + |
| 53. | W029 | + | + |
| 54. | W032 | + | + |
| 55. | W032 | + | + |
| 56. | W032 | + | + |
| 57. | W032 | + | + |
| 58. | W032 | + | + |
| 59. | W032 | + | + |
| 60. | W041 | + | + |
| 61. | W056 | + | + |
| 62. | W060 | + | + |
| 63. | W068 | + | + |
| 64. | W075 | + | + |
| 65. | W135 | + | + |

*Cut-off value for assay of invention: 0.98 µg/ml
**Cut-off value for assay of U.S. Pat. No. 4,376,110

Both assays detected all late stage breast cancer patients as positive and none as negative. The assay of the invention, in addition, showed none of the normal female sere as positive whereas the assay in accordance with U.S. Pat. No. 4,376,110 showed 3 of the normal female sera as positive which should have been negative. Thus, based on the assay of U.S. Pat. No. 4,376,110, the samples of these 3 normal females were labeled as having breast cancer when in fact they were from normal females. These samples are all considered false positives. These 3 women had no evidence of breast cancer, were healthy and continued to be so. Therefore, out of 40 normal sera, the assay in accordance with U.S. Pat. No. 5,376,110 detected 3 false positives. The sensitivity and specificity of the two assays were for late stage breast cancer patients were calculated as described above and are shown is Table 10 below.

TABLE 10

Sensitivity and Specificity of Assays of
Invention and U.S. Pat. No. 4,376,110

|  | Assay of Invention | U.S. patent '110 Assay |
|---|---|---|
| Sensitivity | 100% | 100% |
| Specificity | 100% | 92% |

The above results indicate that the assay according to U.S. Pat. No. 4,376,110 gives 8% false positives while the assay of the invention gives no false positives. These false positive values decrease the specificity of the assay according to U.S. Pat. No. 5,376,110 to 92% when compared with a 100% specificity for the assay of the invention.

The assay according to U.S. Pat. No. '110, therefore, has a significantly high number of false positives (8%) when compared with the assay of the invention (0%). This is in accordance with the disclosure of the Centocor® brochure accompanying the kit sold for practicing the assay of the prior art patent.

Example 22

Statistical Significance of Results

The antigen levels' distributions in the normal women's samples were determined for the assay of the invention and that of U.S. Pat. No. 5,376,110. These were calculated by the Kolmogorov-Smirnov statistical approach based on the empirical distribution function of the samples (Hawkins, C. A., & Weber, J. E., Statistical Analysis, P. 546, Harper & Row Publishers, N.Y., (1980)). This approach addresses the issue of whether or not the distribution of the results of the two assays is the same or not at the 5% error level.

The cumulative probabilities were computed for both groups of results. Thereafter, the two cumulative probabilities were subtracted from one another and the maximum difference (D) obtained.

The D value obtained by applying the above statistical analysis was 0.35. The critical value for D is 0.30. Any value of D above this value can be said to represent two different populations. Thus, the results obtained by the assay of U.S. Pat. No. 5,376,110 correspond to a different population than the one represented by the present assay and the actual population screened ($p \leq 0.05$).

The statistical results obtained in (10) above indicate that the present assay and that of U.S. Pat. No. 4,376,110 represent two separate and distinct populations, the present assay showing a 100% correspondence with the real group of normal women as shown from the follow-up studies of the actual women's group and the U.S. Pat. No. 5,376,110 assay showing, at an error of 5%, that it, in fact, provides a distorted view of the population to the extent that it appears to be a different population.

The statistical analysis was not applied to the female breast cancer patient groups because both assays showed the same results.

The invention now being fully described, it will be apparent to one of ordinary skill in the art that many changes and modifications can be made thereto without departing from the spirit or scope of the invention as set forth therein.

What is claimed as novel and useful in Letters Patent of the United States is:

1. A fusion protein comprising a first peptide comprising an amino acid sequence or 1–10,000 repeats of an amino acid sequence, wherein said amino acid sequence is selected from the group consisting of SEQ. ID NO:4, SEQ. ID NO:6, SEQ. ID NO:7, SEQ. ID NO:8, SEQ. ID NO:9, SEQ. ID NO:10, SEQ. ID NO:12, SEQ. ID NO:13, SEQ. ID NO:14, SEQ. ID NO:15, SEQ. ID NO:16, SEQ. ID NO:17, SEQ. ID NO:18, SEQ. ID NO:19, SEQ. ID NO:20, SEQ. ID NO:21, SEQ. ID NO:22, SEQ. ID NO:23, SEQ. ID NO:24, SEQ. ID NO:25, SEQ. ID NO:26, SEQ. ID NO:27, SEQ. ID NO:28, SEQ. ID NO:29, SEQ. ID NO:30, SEQ. ID NO:31, SEQ. ID NO:32, and SEQ. ID NO:33; and a second peptide of at least 3 amino acids, which substantially fail to bind to human milk fat globule (HMFG) specific antibody; the fusion protein being at least 6 amino acids long.

2. The fusion protein of claim 1, wherein the first peptide has up to about 30–600 amino acids, and the second peptide has up to about 10,000 amino acids.

3. The fusion protein of claim 2, wherein the first peptide has at least about 6 amino acids, and the second peptide has at least about 5 to 600 amino acids.

4. The fusion protein of claim 1, which is non-denatured.

5. The fusion protein of claim 1, wherein the first peptide comprises an amino acid sequence selected from the group consisting of SEQ. ID NO:4, SEQ. ID NO:6, SEQ. ID NO:7, SEQ. ID NO:8, SEQ. ID NO:9, SEQ. ID NO:10, SEQ. ID NO:12, SEQ. ID NO:13, SEQ. ID NO:14, SEQ. ID NO:15, SEQ. ID NO:16, SEQ. ID NO:17, SEQ. ID NO:18, SEQ. ID NO:19, SEQ. ID NO:20, SEQ. ID NO:21, SEQ. ID NO:22, SEQ. ID NO:23, SEQ. ID NO:24, SEQ. ID NO:25, SEQ. ID NO:26, SEQ. ID NO:27, SEQ. ID NO:28, SEQ. ID NO:29, SEQ. ID NO:30, SEQ. ID NO:31, SEQ. ID NO:32, and SEQ. ID NO:33.

6. The fusion protein of claim 1, wherein the second peptide comprises β-galactosidase or a fragment of β-galactosidase.

7. The fusion protein of claim 1, wherein the first peptide comprises SEQ. ID NO:4, or tandem repeats of SEQ. ID NO:4.

8. The fusion protein of claim 1, wherein the first peptide comprises SEQ. ID NO:12, or tandem repeats of SEQ. ID NO:12.

9. The fusion protein of claim 1, wherein the first peptide comprises SEQ. ID NO:6 or tandem repeats of SEQ. ID NO:6.

10. The fusion protein of claim 1, comprising HisThrArgProAlaLeu (SEQ. ID NO:10), or tandem repeats of SEQ. ID NO:10.

11. The fusion protein of claim 1, wherein the first peptide comprises SEQ. ID NO:7, or tandem repeats of SEQ. ID NO:7.

12. The fusion protein of claim 1, wherein the first peptide comprises SEQ. ID NO:8, or tandem repeats of SEQ. ID NO:8.

13. The fusion protein of claim 1, wherein the first peptide comprises SEQ. ID NO:9, or tandem repeats of SEQ. ID NO:9.

14. The fusion protein of claim 1, wherein the first peptide comprises SEQ. ID NO:13, or tandem repeats of SEQ. ID NO:13.

15. The fusion protein of claim 1, wherein the first peptide comprises SEQ. ID NO:36, or tandem repeats of SEQ. ID NO:36.

16. A composition comprising the fusion protein of claim 1, and a diluent or carrier.

17. The composition of claim 16, wherein the diluent or carrier comprises a biologically acceptable carrier.

18. The composition of claim 16, wherein the diluent or carrier comprises a pharmaceutically acceptable carrier.

19. A method of producing the fusion protein of claim 1, comprising culturing host cells transfected with a DNA encoding the fusion protein in an expression medium under conditions effective for expression of the protein; and allowing the expression of the fusion protein.

20. The method of claim 19, further comprising, prior to culturing the host cells, transfecting the host cells with a vector comprising a DNA segments encoding the first and second peptides;

allowing the expression of the fusion protein;

selecting a host cell expressing the fusion protein; and allowing the host cell to grow and produce a plurality of host cells.

21. The method of claim 19, further comprising separating the host cells from the fusion protein.

22. The method of claim 20, further comprising prior to transfection, cloning DNA segments encoding the first and second peptides into an expression vector in reading frame with respect to the vector.

23. The method of claim 22, further comprising prior to cloning, obtaining a DNA segment encoding the second peptide;

obtaining an antibody selectively binding at least one of the HMFG differentiation antigen(s);

screening peptides expressed by a DNA library, which bind the antibody; and selecting any DNA fragments which encode peptides that bind the antibody.

* * * * *